US007795389B2

(12) United States Patent
Sun et al.

(10) Patent No.: US 7,795,389 B2
(45) Date of Patent: Sep. 14, 2010

(54) ANTAGONIZING TGF-BETA ACTIVITY WITH VARIOUS ECTODOMAINS TGF-BETA RECEPTORS USED IN COMBINATION OR AS FUSION PROTEINS

(75) Inventors: LuZhe Sun, San Antonio, TX (US); Andrew P. Hinck, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 118 days.

(21) Appl. No.: 11/238,172

(22) Filed: Sep. 28, 2005

(65) Prior Publication Data

US 2007/0244042 A1 Oct. 18, 2007

Related U.S. Application Data

(60) Provisional application No. 60/613,992, filed on Sep. 28, 2004.

(51) Int. Cl.
*C07K 14/00* (2006.01)
*A61K 38/00* (2006.01)
*A61K 38/16* (2006.01)

(52) U.S. Cl. ............................ 530/350; 514/2; 514/12; 424/198.1

(58) Field of Classification Search ....................... None
See application file for complete search history.

(56) References Cited

U.S. PATENT DOCUMENTS

| | | | | |
|---|---|---|---|---|
| 5,118,791 A | | 6/1992 | Burnier et al. | 530/326 |
| 5,616,561 A | | 4/1997 | Barcellos-Hoff | 514/13 |
| 5,693,607 A | * | 12/1997 | Segarini et al. | 514/2 |
| 2002/0004037 A1 | | 1/2002 | Koteliansky et al. | 514/12 |

FOREIGN PATENT DOCUMENTS

| | | |
|---|---|---|
| WO | WO 00/20449 | 4/2000 |
| WO | WO 00/20591 | 4/2000 |
| WO | WO 00/20607 | 4/2000 |
| WO | WO 01/12670 | 2/2001 |
| WO | WO 01/92298 | 12/2001 |
| WO | WO 02/04479 | 1/2002 |
| WO | WO 02/085942 | 10/2002 |

OTHER PUBLICATIONS

Lin et al., J. Biol. Chem., 1995, 270(6):2747-2754.*
Bandyopadhyay et al., Cancer Res., 1999, 59:5041-5046.*
Lopez-Casillas et al., J. Cell Biol., 1994, 124(4):557-568.*
Watson et al., 2005, Curr. Opin. Struc. Biol., 15(3):275-285.*
Hart et al., Nature Struc. Biol., 2002, 9(3):203-208.*
Kirsch et al., EMBO J., 2000, 19(13):3314-3324.*
Adler et al., "Elevated levels of circulating interleukin-6 and transforming growth factor-β1 in patients with metastatic prostatic carcinoma," *J. Urol.*, 161:182-187, 1999.
Arteaga et al., "The multifunctional role of transforming growth factor (TGF)-betas on mammary epithelial cell biology," *Breast Cancer Res. Treat.*, 38(1):49-56, 1996.
Bandyopadhyay et al, "A soluble transforming growth factor β type III receptor suppresses tumorigenicity and metastasis of human breast cancer MDA-MB-231 cells," *Cancer Res.*, 59(19):5041-5046, 1999.
Bandyopadhyay et al., "Antitumor activity of a recombinant soluble betaglycan in human breast cancer xenograft," *Cancer Res.*, 62(16):4690-4695, 2002.
Bandyopadhyay et al., "Extracellular domain of TGFβ type III receptor inhibits angiogenesis and tumor growth in human cancer cells," *Oncogene*, 21(22):3541-3551, 2002.
Blobe et al., "Role of transforming growth factor β in human disease," *N. Engl. J. Med.*, 342(18):1350-1358, 2000.
Bonewald and Mundy, "Role of transforming growth factor- β in bone remodeling," *Clin. Orthop. Relat. Res.*, 261-276, 1990.
Chen et al., "Expression of transforming growth factor β beta (TGFβ) type III receptor restores autocrine $TGF\beta_1$ activity in human breast cancer MCF-7 cells," *J. Biol. Chem.*, 272(19):12862-12867, 1997.
Derynck, "TGF-β-receptor-mediated signaling," *Trends Biochem. Sci.*, 19(12):548-553, 1994.
Fajardo et al., "Transforming growth factor β1 induces angiogenesis in vivo with a threshold pattern," *Lab. Invest.*, 74:600-608, 1996.
Fukushima et al., "Localization of transforming growth factor β binding site in betaglycan. Comparison with small extracellular matrix proteoglycans," *J. Biol. Chem.*, 268(30):22710-22715, 1993.
Koeneman et al., "Osteomimetic properties of prostate cancer cells: a hypothesis supporting the predilection of prostate cancer metastasis and growth in the bone environment," *Prostate*, 39(4):246-261, 1999.
Lee et al., "Transforming growth factor- β in benign and malignant prostate," *Prostate*, 39(4):285-290, 1999.
Lei et al., "Autocrine TGFβ supports growth and survival of human breast cancer MDA-MB-231 cells," *Oncogene*, 21(49):7514-7523, 2002.
Lin et al., "The soluble exoplasmic domain of the type II transforming growth factor (TGF)-β receptor. A heterogeneously glycosylated protein with high affinity and selectivity for TGF-β ligands," *J. Biol. Chem.*, 270(6):2747-2754, 1995.
López-Casillas et al., "Betaglycan can act as a dual modulator of TGF-β access to signaling receptors: mapping of ligand binding and GAG attachment sites," *J. Cell Biol.*, 124:557-568, 1994.
López-Casillas et al., "Betaglycan presents ligand to the TGFβ signaling receptor," *Cell*, 73(7):1435-1444,1993.
Lyons and Moses, "Transforming growth factors and the regulation of cell proliferation," *Eur. J. Biochem.*, 187(3):467-473, 1990.

(Continued)

*Primary Examiner*—Elizabeth C. Kemmerer
*Assistant Examiner*—Xiaozhen Xie
(74) *Attorney, Agent, or Firm*—Fulbright & Jaworski LLP

(57) ABSTRACT

Anti-cancer agents and/or transforming growth factor beta (TGF-beta or TGFβ) antagonists are disclosed, where the agents and/or antagonists include a therapeutically effective amount of a combination of therapeutically active portions of sRII and therapeutically active portions of sRIII or a fusion polypeptide or protein comprising therapeutically active portions of sRII and therapeutically active portions of sRIII. Methods for preventing, treating and/or ameliorating the symptoms of cancer are also disclosed based on administering an effective amount of a composition of this invention.

8 Claims, 4 Drawing Sheets

OTHER PUBLICATIONS

Markowitz and Roberts, "Tumor suppressor activity of the TGF-β pathway in human cancers," *Cytokine Growth Factor Rev.*, 7:93-102, 1996.

Massagué and Chen, "Controlling TGF-β signaling," *Genes & Development*, 14(6):627-644, 2000.

Massagué et al., "TGFβ signaling in growth control, cancer, and heritable disorders," *Cell*, 103(2):295-309, 2000.

Massagué, "The transforming growth factor-β family," *Annu. Rev. Cell Biol.*, 6:597-641, 1990.

Miyazono et al., "Signal transduction via serine/threonine kinase receptors," *Semin. Cell Biol.*, 5(6):389-398, 1994.

Piek et al., "Specificity, diversity, and regulation in TGF-beta superfamily signaling," *FASEB J.*, 13(15):2105-2124, 1999.

Reiss, "TGF-β and cancer," *Microbes and Infection*, 1(15):1327-1347, 1999.

Roberts and Sporn, "The transforming growth factor-βs," in: *Peptide growth factors and their receptors*, pp. 419-472, 1991.

Roberts and Wakefield, "The two faces of transforming growth factor β in carcinogenesis," *Proc. Natl. Acad. Sci. U.S.A.*, 100(15):8621-8623, 2003.

Shariat et al., "Preoperative plasma levels of transforming growth factor $\beta_1$ (TGF-$\beta_1$) strongly predict progression in patients undergoing radical prostatectomy," *J. Clin. Oncol.*, 19(11):2856-2864, 2001.

Sosroseno and Herminajeng, "The immunoregulatory roles of transforming growth factor β," *Br. J. Biomed. Sci.*, 52(2):142-148, 1995.

Sun, "Tumor-suppressive and promoting function of transforming growth factor β," *Front Biosci.*, 9:1925-1935, 2004.

Vilchis-Landeros et al., "Recombinant soluble betaglycan is a potent and isoform-selective transforming growth factor-β neutralizing agent," *Biochem. J.*, 355(Pt. 1):215-222, 2001.

Wang et al., "Development of gene-switch transgenic mice that inducibly express transforming growth factor β1 in the epidermis," *Proc. Natl. Acad. Sci. U.S.A.*, 96(15):8483-8488, 1999.

Wang et al., "Expression cloning and characterization of the TGF-β type III receptor," *Cell*, 67(4):797-805, 1991.

Wrana et al., "Mechanism of activation of the TGF-β receptor," *Nature*, 370(6488):341-347, 1994.

Yang and Moses, "Transforming growth factor β1 -induced changes in cell migration, proliferation, and angiogenesis in the chicken chorioallantoic membrane," *J. Cell Biol.*, 111(2):731-741, 1990.

Yin et al., "TGF-β signaling blockade inhibits PTHrP secretion by breast cancer cells and bone metastases development," *J. Clin. Invest.*, 103(2):197-206, 1999.

* cited by examiner

ANTAGONIZING TGF-BETA ACTIVITY WITH VARIOUS ECTODOMAINS TGF-BETA RECEPTORS USED IN COMBINATION OR AS FUSION PROTEINS

RELATED APPLICATIONS

This application claims provisional priority to U.S. Provisional Patent Application Ser. No. 60/613,992, filed 28 Sep. 2004, incorporated herein by reference.

GOVERNMENT RIGHTS

This invention was made with government support under grant number CA79683 awarded by the National Institutes of Health/National Cancer Institute, grant number DAMD 17-03-1-0133 awarded by the U.S. Department of Defense/U.S. Army, and grant number GM58670 awarded by the National Institutes of Health/National Institute of General Medical Sciences. The government has certain rights in the invention.

BACKGROUND OF THE INVENTION

1. Field of the Invention

The present invention relates to transforming growth factor beta (TGF-beta or TGFβ) antagonists and method for treating or ameliorating symptoms of cancer and other human diseases including therapeutically active portions of at least two soluble TGF isoform receptors.

More particularly, the present invention relates to TGF-beta antagonists and method for treating or ameliorating symptoms of cancer and other human diseases, where the TGF-beta antagonists include a mixture or combination of therapeutically active portions of sRII and therapeutically active portions of sRIII and/or to a fusion protein including therapeutic portions of sRII and/or sRIII and the method includes administering to an animal including a human a therapeutically active amount of the combination.

2. Description of the Related Art

TGFβ, its Signal Transduction and its Function. Transforming growth factor beta (TGFβ) isoforms, named β1, β2, and β3 from mammals, are homodimeric polypeptides of 25 kDa. They are secreted in a latent form and only a small percentage of total secreted TGFβs is activated under physiological conditions. TGFβ binds to three different cell surface receptors called type I (RI), type II (RII) and type III (RIII) receptors. RIII (also called betaglycan) has two TGFβ binding sites in its extracellular domain, which are called the E and U domains. It can sequester and present the ligand to RII to augment TGFβ activity when it is membrane-bound (Chen et al., 1997; Lopez-Casillas et al., 1993; Wang et al., 1991; Fukushima et al., 1993; Lopez-Casillas et al., 1994). TGFβ1 and TGFβ3 can bind RII with high affinity; however, TGFβ2 requires RIII for binding to RII. RI and RII are serine/threonine kinase receptors. Binding of TGFβ to RII recruits and activates RI through phosphorylation (Wrana et al., 1994). The activated RI phosphorylates intracellular Smad2 and Smad3, which then interact with Smad4 protein to regulate gene expression in the nucleus (Piek et al., 1999; Massague and Chen, 2000). Through its regulation of gene expression, TGFβ has been shown to influence many cellular functions such as cell proliferation, differentiation, cell-cell and cell-matrix adhesion, cell motility, and activation of lymphocytes (Massague, 1990; Roberts and Spom, 1991). TGFβ has also been shown or implicated to induce or mediate the progression of many diseases such as osteoporosis, hypertension, atherosclerosis, hepatic cirrhosis and fibrotic diseases of the kidney, liver and lung (Blobe et al., 2000). Perhaps, the most extensively studied function of TGFβ is its role in tumor progression as summarized below.

Loss of TGFβ's Growth Inhibitory Activity During Tumor Progression. TGFβs have been shown to be potent growth inhibitors in various cell types including epithelial cells (Lyons and Moses, 1990). The mechanism of the growth inhibition by TGFβ is mainly due to the regulation of cell cycle-related proteins (Derynck, 1994; Miyazono et al., 1994). Thus, aberrant regulation of cell cycle machinery such as loss of retinoblastoma gene product during tumorigenesis can lead to loss of growth inhibition by TGFβ. Furthermore, mutational inactivation of TGFβ receptors, Smad2 and Smad4 has been reported in various carcinomas (Massague et al., 2000). For example, loss of RI and/or RII expression is often observed in some human gastrointestinal cancers (Markowitz and Roberts, 1996).

TGFβ's Tumor-promoting Activity. While many carcinoma cells lose response to TGFβ's growth inhibition, they often overproduce active TGFβ isoforms when compared to their normal counterpart (Reiss, 1999). This is likely to result in the selection of cancer cells that are resistant to TGFβ's growth inhibitory activity. Indeed, an increased level of TGFβ1 is strongly associated with the progression of many types of malignancies and poor clinical outcome (Reiss, 1999). For example, serum TGFβ1 levels have been shown to correlate to tumor burden, metastasis, and serum prostate specific antigen (PSA) in prostate cancer patients (Adler et al., 1999; Shariat et al., 2001). Consistent with these observations, marked increase of TGFβ1 and TGFβ2 expression was observed in an aggressive androgen-independent human prostate cancer cell line when compared to its less aggressive androgen-dependent parent cell line, LNCap (Patel et al., 2000).

Several mechanisms are believed to mediate TGFβ's tumor-promoting activity (Arteaga et al., 1996; Reiss, 1999). TGFβ is a potent immune suppressor (Sosroseno and Herminajeng, 1995). Overexpression of TGFβ1 in the rat prostate cancer cells was associated with a reduced immune response during tumor formation suggesting that TGFβ may suppress host immune response to the growing tumor (Lee et al., 1999). TGFβ has also been shown to be angiogenic in vivo (Fajardo et al., 1996; Yang and Moses, 1990; Wang et al., 1999). Overexpression of TGFβ during cancer progression is often associated with increased angiogenesis and metastasis suggesting that TGFβ may promote metastasis by stimulating tumor blood vessel formation (Roberts and Wakefield, 2003). TGFβ also plays an important role in promoting bone metastasis of human prostate and breast cancers (Koeneman et al., 1999; Yin et al., 1999). Both TGFβ1 and TGFβ2 are produced by bone tissue, which is the largest source of TGFβ in the body (Bonewald and Mundy, 1990). The latent TGFβ can be activated by proteases such as PSA and urokinase plasminogen activator, which are abundantly secreted by cancer cells (Koeneman et al., 1999). Taken together, TGFβ can act in tumor microenvironment to promote carcinoma growth, angiogenesis and metastasis.

Development of TGFβ Antagonists. Because of its involvement in the progression of various diseases, TGFβ has been targeted for the development of novel therapeutic strategies. One way of antagonizing TGFβ activity is to utilize the ecto-domain of TGFβ type II receptor or type III receptor, also known as betaglycan (BG). We have previously shown that ectopic expression of a soluble BG (sBG, also called sRIII) containing the whole ecto-domain of BG in human carcinoma cell lines can significantly inhibit tumor growth, angiogenesis, and metastasis when they are inoculated in athymic nude mice (Bandyopadhyay et al., 1999; Bandyopadhyay et al., 2002b). More recently, we have shown that systemic administration of a recombinant sBG can also inhibit the growth, angiogenesis and metastasis of the xenografts of human breast carcinoma MDA-MB-231 cells in nude mice (Bandyopadhyay et al., 2002a). However, the inhibition was only partial, not complete. This could be due in part to the fact that both active TGFβ1 and TGFβ2 were produced by the cells and the anti-TGFβ potency of sBG is 10-fold lower for TGFβ1 than for TGFβ2 (Vilchis-Landeros et al., 2001). Interestingly, while the extracellular domain of RII (sRII) has very low affinity for TGFβ2, its affinity for TGFβ1 and TGFβ3 is more than ten times higher than that of sBG (Lin et al., 1995; Vilchis-Landeros et al., 2001).

While numerous TGF antagonists have been prepared and tested, all have less than complete TGF isoform inhibiting properties. Thus, there is a need in the art for a class of generalized TGF antagonists or inhibitors which can inhibit all three isoforms of TGF, simultaneously.

SUMMARY OF THE INVENTION

Generic TGF-Beta Antagonists

The present invention provides TGF-beta antagonists including a therapeutically effective amount of a mixture or combination of two or more of: (1) therapeutically active portions of soluble cell surface type II receptors (sRII); (2) therapeutically active portions of soluble cell surface type III receptors (sRIII); (3) a fusion polypeptide or protein comprising therapeutically active portions of sRII or synthetic analogs thereof; (4) a fusion polypeptide or protein comprising therapeutically active portions of sRIII or synthetic analogs thereof; and (5) a fusion polypeptide or protein comprising therapeutically active portions of sRII and therapeutically active portions of sRIII or synthetic analogs thereof. The term synthetic analogs means fusion polypeptide or proteins where one or more native amino acid in the active portions of sRII and sRIII are replace by a naturally occurring or synthetic amino acid that does not render the portions inactive. Such amino acid substitutions are well known in the art. The term therapeutically active amount means a dose between about 50 nmole/kg every other day and about 200 nmole/kg/day of any of the compositions of this invention.

Combinational TGF-Beta Antagonists

The present invention provides TGF-beta antagonists including a therapeutically effective amount of a mixture or combination of therapeutically active portions of sRII and therapeutically active portions of sRIII.

The present invention also provides TGF-beta antagonists including a therapeutically effective amount of a mixture or combination of two or more of therapeutically active portions of sRII, therapeutically active portions of an E domain of sRIII, or therapeutically active portions of an U domain of sRIII.

The present invention also provides TGF-beta antagonists including a therapeutically effective amount of a mixture or combination of therapeutically active portions of sRII and therapeutically active portions of an E domain of sRIII.

The present invention also provides TGF-beta antagonists including a therapeutically effective amount of a mixture or combination of therapeutically active portions of sRII and therapeutically active portions of an U domain of sRIII.

The present invention also provides TGF-beta antagonists including a therapeutically effective amount of therapeutically active portions of sRII and a mixture or combination of therapeutically active portions of an E domain of sRIII and therapeutically active portions of an U domain of sRIII.

Fusion Polypeptide or Protein TGF-Beta Antagonists

The present invention also provides TGF-beta antagonists including a therapeutically effective amount of a fusion polypeptide or protein comprising therapeutically active portions of sRII and therapeutically active portions of sRIII.

The present invention also provides TGF-beta antagonists including a therapeutically effective amount of a fusion polypeptide or protein comprising therapeutically active portions of sRII and therapeutically active portions of an E domain of sRIII and/or therapeutically active portions an U domain of sRIII.

The present invention also provides TGF-beta antagonists including a therapeutically effective amount of a fusion polypeptide or protein comprising therapeutically active portions of sRII and therapeutically active portions of an E domain of sRIII.

The present invention also provides TGF-beta antagonists including a therapeutically effective amount of a fusion polypeptide or protein comprising therapeutically active portions of sRII and therapeutically active portions of an U domain of sRIII.

The present invention also provides TGF-beta antagonists including a therapeutically effective amount of a fusion polypeptide or protein comprising therapeutically active portions of sRII and therapeutically active portions of an E domain of sRIII and therapeutically active portion of an U domain of sRIII.

The present invention also provides TGF-beta antagonists including a therapeutically effective amount of therapeutically active portions of sRII and a fusion polypeptide or protein comprising therapeutically active portions of an E domain of sRIII and therapeutically active portions of an U domain of sRIII.

Generic Anti-Cancer Agents

The present invention provides TGF-beta antagonists including a therapeutically effective amount of a mixture or combination of two or more of: (1) therapeutically active portions of soluble cell surface type II receptors (sRII); (2) therapeutically active portions of soluble cell surface type III receptors (sRIII); (3) a fusion polypeptide or protein comprising therapeutically active portions of sRII or synthetic analogs thereof; (4) a fusion polypeptide or protein comprising therapeutically active portions of sRIII or synthetic analogs thereof; and (5) a fusion polypeptide, protein or synthetic analogs thereof comprising therapeutically active portions of sRII and therapeutically active portions of sRIII or synthetic analogs thereof alone or in combination with any other anti-cancer composition known in the art.

Combinational Anti-Cancer Agents

The present invention provides TGF-beta antagonists including a therapeutically effective amount of a combination of therapeutically active portions of sRII and therapeutically active portions of sRIII alone or in combination with any other anti-cancer composition known in the art.

The present invention also provides TGF-beta antagonists a therapeutically effective amount of a combination of therapeutically active portions of sRII and therapeutically active portions of an E domain of sRIII, and/or therapeutically active portions of an U domain of sRIII alone or in combination with any other anti-cancer composition known in the art.

The present invention also provides TGF-beta antagonists including a therapeutically effective amount of a combination of therapeutically active portions of sRII and therapeutically active portions of an E domain of sRIII alone or in combination with any other anti-cancer composition known in the art.

The present invention also provides TGF-beta antagonists including a therapeutically effective amount of a combination of therapeutically active portions of sRII and therapeutically active portions of an U domain of sRIII alone or in combination with any other anti-cancer composition known in the art.

The present invention also provides TGF-beta antagonists including a therapeutically effective amount of a combination of therapeutically active portions of sRII and of a mixture or combination therapeutically active portions E domain of sRIII and therapeutically active U domain of sRIII alone or in combination with any other anti-cancer composition known in the art.

Fusion Polypeptide or Protein Anti-Cancer Agents

The present invention also provides TGF-beta antagonists including a therapeutic effective amount of a fusion polypeptide or protein comprising therapeutically active portions of sRII and therapeutically active portions of sRIII alone or in combination with any other anti-cancer composition known in the art.

The present invention also provides TGF-beta antagonists including a therapeutic effective amount of a fusion polypeptide or protein comprising therapeutically active portions of sRII and therapeutically active portions of an E domain of sRIII, and/or therapeutically active portions of an U domain of sRIII alone or in combination with any other anti-cancer composition known in the art.

The present invention also provides TGF-beta antagonists including a therapeutic effective amount of a fusion polypeptide or protein comprising therapeutically active portions of sRII and therapeutically active portions of an E domain of sRIII alone or in combination with any other anti-cancer composition known in the art.

The present invention also provides TGF-beta antagonists including a therapeutic effective amount of a fusion polypeptide or protein comprising therapeutically active portions of sRII and therapeutically active portions of an U domain of sRIII alone or in combination with any other anti-cancer composition known in the art.

The present invention also provides TGF-beta antagonists including a therapeutic effective amount of a fusion polypeptide or protein comprising therapeutically active portions of sRII and of a mixture or combination therapeutically active portions E domain of sRIII and therapeutically active U domain of sRIII alone or in combination with any other anti-cancer composition known in the art.

The present invention also provides TGF-beta antagonists including a therapeutically effective amount of therapeutically active portions of sRII and a fusion polypeptide or protein comprising therapeutically active portions of an E domain of sRIII and therapeutically active portions of an U domain of sRIII alone or in combination with any other anti-cancer composition known in the art.

Methods for Treating, Preventing and/or Ameliorating Cancers

The present invention also provides methods for preventing, treating and/or ameliorating symptoms of cancer including the step of administering to an animal including a human a therapeutically effective amount of any of the compositions of this invention, where the administrating can be oral, intravenous, intra-arterial, direct or a mixture or combination thereof and can be a single dose, periodic doses, intermittent doses, continuous dosing or mixture or combination thereof.

DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
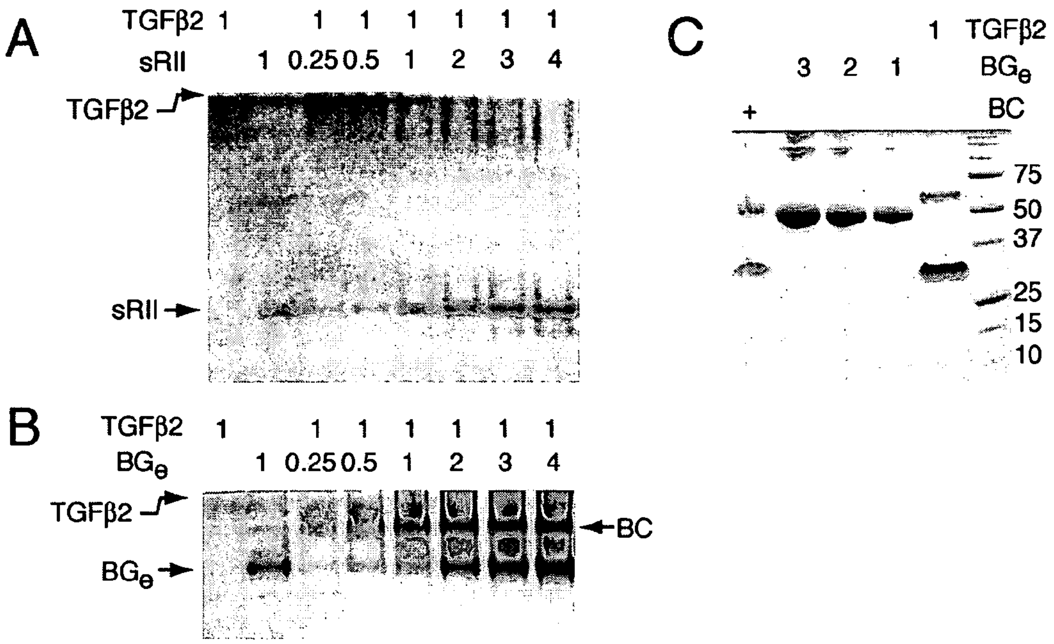
FIGS. 1A-C depict binding of the E-domain of betaglycan ($BG_e$) and the TGFβ type II receptor extracellular domain (sRII) to TGFβ2.

The inventors have found that broad application TGF antagonists that include a therapeutically effective amount of a combination of therapeutically active portions of sRII and therapeutically active portions of sRIII or a fusion polypeptide or protein comprising therapeutically active portions of sRII and therapeutically active portions of sRIII, where a therapeutically active amount of the products and/or fusion proteins of this invention is a dose between about 25 nmole/kg and about 200 nmole/kg on an individual basis or between about 25 nmole/kg/day and about 200 nmole/kg/day or between about 25 nmole/kg every other day to about 200 nmole/kg/day. Preferably, a therapeutically active amount of the products and/or fusion proteins of this invention is a dose between about 50 nmole/kg and about 200 nmole/kg on an individual basis or between about 25 nmole/kg/day and about 200 nmole/kg/day or between about 50 nmole/kg every other day to about 200 nmole/kg/day.

Since many tumor cells and tissues contain both TGFβ1 and TGFβ2, the inventors found that a soluble receptor with an equally high affinity for both TGFβ isoforms can be prepared that is more effective in antagonizing TGFβ's tumor-promoting activity than sBG. The inventors have tested the anti-TGFβ activity of a combination of sRII and an E domain of sBG, BGe. The inventors have also constructed an expression plasmid containing a fusion protein of sRII+BGe. In addition, the inventors have also constructed expression plasmids for sRII plus sBG, and sRII plus BGu, the U-domain of BG.

Broadly, the present invention relates to compositions including a therapeutically effective amount of a combination of therapeutically active portions of sRII and therapeutically active portions of sRIII or a fusion polypeptide or protein comprising therapeutically active portions of sRII and therapeutically active portions of sRIII, where the compounds inhibit, reduce, interfere with the tumor promoting properties of any isoform of TGFβ.

The compositions of this invention based on a combination of active portions of sRII and sRIII (sBG) can include equal concentrations of therapeutically active portions of sRII and sRIII or the compositions can comprise unequal concentrations of therapeutically active portions sRII and sRIII. The actual concentration variability of these two components may well vary depending on the nature of the cancer, but any concentration mix is contemplated by the present invention. Thus, the composition can include between about 5 wt. % and about 95 wt. % of therapeutically active portions sRII and between about 95 wt. % and about 5 wt. % therapeutically active portions sRIII. It should also be recognized that the combination may include differing amounts of different therapeutically active portions of sRII and sRIII also known as sBG.

The compositions of this invention based on a fusion protein or polypeptide of active portions of sRII and sRIII (sBG) can include at least one polypeptide sequence comprising a therapeutically active portion of sRII and at least one polypeptide sequence comprising a therapeutically active portion of sRIII (sBG). However, the fusion protein can also include: (1) a plurality of polypeptide sequences comprising a therapeutically active portion of sRII and at least one polypeptide sequence comprising a therapeutically active portion of sRIII (sBG); (2) at least one polypeptide sequence comprising a therapeutically active portion of sRII and a plurality of polypeptide sequences comprising a therapeutically active portion of sRIII (sBG); or a plurality of polypeptide sequences comprising a therapeutically active portion of sRII and a plurality of polypeptide sequences comprising a therapeutically active portion of sRIII (sBG). The fusion proteins can also include non-active spacers interposed between the active sequences of therapeutically active portions of sRII and sRIII. The present invention also includes the plasmids or DNA encoding sequences corresponding to the desired fusion protein. The plasmids or DNA encoding sequences can include promoters, multiple reading frames, multiple repeating peptide sequences.

The published crystal structure of sRII in complex with TGFβ3 (Hart, P. J., Deep, S., Taylor, A. B., Shu, Z., Hinck, C. S., & Hinck, A. P. (2002) "Crystal structure of the human TGF-β3-TβR2 ectodomain complex" Nature Structural Biol., 9, 203-208). The crystal structure showed, of course, which residues in sRII contact TGFβ. Therefore, we believe that the therapeutically active portions of sRII will include these binding amino acids and sufficient amino acids around that sites to maintain the structural context of the protein. The following three sequences represent at least some of portions of sRII that we believe will be therapeutically active sequences of sRII, including the sequences containing amino acids involved in the binding of TGFβ3:

A.

(SEQ ID NO. 11)

MIPPHVQKSV NNDMIVTDNN GAVKFPQ*L*CK *F*C*D*VRFSTCD

NQKSCMSNCS

B.

(SEQ ID NO. 12)

*ITSI*C*E*PQE VCVAVWRKND ENITLETVCH DPKLPYHDFI

LEDAASPKCI

C.

(SEQ ID NO. 13)

MKEKKKPGET FFMCSCSS*DE*CNDNIIFSEE YNTSNPD where the emboldened amino acids are binding amino acids and the emboldened and italics amino acids are critical binding amino acids.

Besides the native protein structures, the present invention also relates to variants of the therapeutically active portion of sRII, sRIII, sRIIIe and sRIIIu, where none essential amino acids are substituted by substitutions that do not greatly change the binding of the TGFβ isoforms. Moreover, the present invention also contemplates synthetic constructs that include the amino acids of sRII, sRIII, sRIIIe and sRIIIu that are instrumental in TGFβ isoforms binding where the amino acids are held structurally in place using synthetic constructs that are known not to induce an immune response.

Suitable anticancer agents for use in conjunction with the compositions of this invention include, without limitation, alkylating agents, antimitotic agents, topoisomerase I inhibitors, topoisomerase II inhibitors, RNA/DNA antimetabolites, DNA antimetabolites, or mixtures or combinations thereof.

Exemplary examples of alkylating agents include, without limitation, Asaley (NSC 167780), AZQ (NSC 182986), BCNU (NSC 409962), Busulfan (NSC 750), carboxyphthalatoplatinum (NSC 271674), CBDCA (NSC 241240), CCNU (NSC 79037), CHIP (NSC 256927), chlorambucil (NSC 3088), chlorozotocin (NSC 178248), cis-platinum (NSC 119875), clomesone (NSC 338947), cyanomorpholinodoxorubicin (NSC 357704), cyclodisone (NSC 348948), dianhydrogalactitol (NSC 132313), fluorodopan (NSC 73754), hepsulfam (NSC 329680), hycanthone (NSC 142982), melphalan (NSC 8806), methyl CCNU (NSC 95441), mitomycin C(NSC 26980), mitozolamide (NSC 353451), nitrogen mustard (NSC 762), PCNU (NSC 95466), piperazine ../drugs/mainator (NSC 344007), piperazinedione (NSC 135758), pipobroman (NSC 25154), porfiromycin (NSC 56410), spirohydantoin mustard (NSC 172112), teroxirone (NSC 296934), tetraplatin (NSC 363812), thio-tepa (NSC 6396), triethylenemelamine (NSC 9706), uracil nitrogen mustard (NSC 34462), Yoshi-864 (NSC 102627), or mixtures or combinations thereof.

Exemplary examples of antimitotic agents include, without limitation, allocolchicine (NSC 406042), Halichondrin B (NSC 609395), colchicine (NSC 757), colchicine derivative (NSC 33410), dolastatin 10 (NSC 376128), maytansine (NSC 153858), rhizoxin (NSC 332598), taxol (NSC 125973), taxol derivative (NSC 608832), thiocolchicine (NSC 361792), trityl cysteine (NSC 83265), vinblastine sulfate (NSC 49842), vincristine sulfate (NSC 67574)

Exemplary examples of Topoisomerase I Inhibitors include, without limitation, camptothecin (NSC 94600), camptothecin, Na salt (NSC 100880), aminocamptothecin (NSC 603071), camptothecin derivative (NSC 95382), camptothecin derivative (NSC 107124), camptothecin derivative (NSC 643833), camptothecin derivative (NSC 629971), camptothecin derivative (NSC 295500), camptothecin derivative (NSC 249910), camptothecin derivative (NSC 606985), camptothecin derivative (NSC 374028), camptothecin derivative (NSC 176323), camptothecin derivative (NSC 295501), camptothecin derivative (NSC 606172), camptothecin derivative (NSC 606173), camptothecin derivative (NSC 610458), camptothecin derivative (NSC 618939), camptothecin derivative (NSC 610457), camptothecin derivative (NSC 610459), camptothecin derivative (NSC 606499), camptothecin derivative (NSC 610456), camptothecin derivative (NSC 364830), camptothecin derivative (NSC 606497), morpholinodoxorubicin (NSC 354646)

Exemplary examples of Topoisomerase II Inhibitors include, without limitation, doxorubicin (NSC 123127), amonafide (NSC 308847), m-AMSA (NSC 249992), anthrapyrazole derivative (NSC 355644), pyrazoloacridine (NSC 366140), bisantrene HCL (NSC 337766), daunorubicin (NSC 82151), deoxydoxorubicin (NSC 267469), mitoxantrone (NSC 301739), menogaril (NSC 269148), N,N-dibenzyl daunomycin (NSC 268242), oxanthrazole (NSC 349174), rubidazone (NSC 164011), VM-26 (NSC 122819), VP-16 (NSC 141540), or mixtures or combinations thereof.

Exemplary examples of RNA/DNA Antimetabolites include, without limitation, L-alanosine (NSC 153353), 5-azacytidine (NSC 102816), 5-fluorouracil (NSC 19893), acivicin (NSC 163501), aminopterin derivative (NSC 132483), aminopterin derivative (NSC 184692), aminopterin derivative (NSC 134033), an antifol (NSC 623017), Baker's soluble antifol (NSC 139105), dichlorallyl lawsone (NSC 126771), brequinar (NSC 368390), ftorafuir (pro-drug) (NSC 148958), 5,6-dihydro-5-azacytidine (NSC 264880), methotrexate (NSC 740), methotrexate derivative (NSC 174121), N-(phosphonoacetyl)-L-aspartate (PALA) (NSC 224131), pyrazofurin (NSC 143095), trimetrexate (NSC 352122), or mixtures or combinations thereof.

Exemplary examples of DNA Antimetabolites include, without limitation, 3-HP (NSC 95678), 2'-deoxy-5-fluorouridine (NSC 27640), 5-HP (NSC 107392), alpha-TGDR (NSC 71851), aphidicolin glycinate (NSC 303812), ara-C (NSC 63878), 5-aza-2'-deoxycytidine (NSC 127716), beta-TGDR (NSC 71261), cyclocytidine (NSC 145668), guanazole (NSC 1895), hydroxyurea (NSC 32065), inosine glycodialdehyde (NSC 118994), macbecin II (NSC 330500), pyrazoloimidazole (NSC 51143), thioguanine (NSC 752), thiopurine (NSC 755), or mixtures or combinations thereof.

Additional information and detailed structural and other types of data can be found at the following web site dtp.nci.nih.gov/docs/cancer/searches/standard_mechanism_list.html#alkyl.

EXPERIMENTAL SECTION

TGFβ2 forms a binary complex with the E-domain of BG or sRIII (BGe or sRIIIe), but not with the extracellular domain of TGFβ type II receptor (sRII).

Consistent with published studies (Lin et al., 1995; Vilchis-Landeros et al., 2001), TGFβ2 and sRII did not form a binary complex when mixed together (FIG. 1A). In contrast, a binary complex was detected in a native polyacryamide gel when TGFβ2 and the E-domain of BG (sRII) were mixed together (FIG. 1B). The complex was found to contain both TGFβ2 and the E-domain in a SDS polyacrylamide gel as shown in FIG. 1C.

Recombinant sRII and sBG (sRIII) antagonize the activity of TGFβ3 and TGFβ2, respectively, in a cell based assay.

Figure 2:
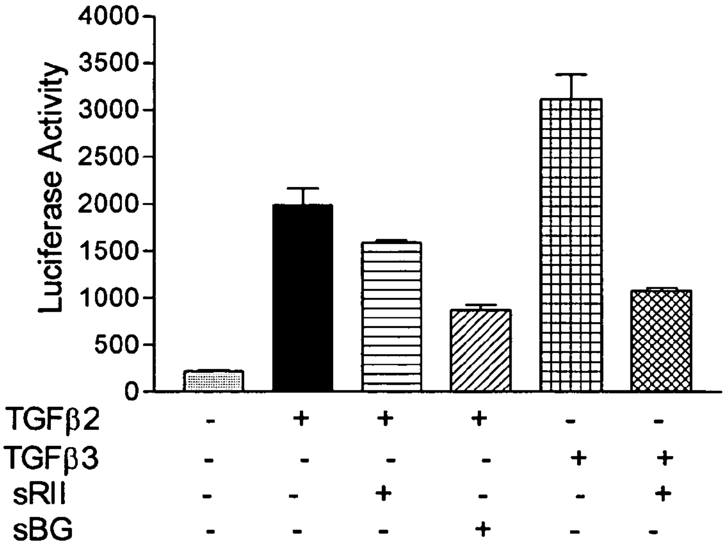
FIG. 2 depicts neutralization of the gene transcription activity of TGFβ2 and TGFβ3 by sBG or sRII respectively.

Consistent with published studies and the data in FIG. 1, recombinant sRII was found to be a much better antagonist against TGFβ3, which has similar binding property to TGFβ1, than against TGFβ2 as shown in FIG. 2. A telomerase-immortalized human mammary epithelial cell line was transiently transfected with a plasmid containing a TGFβ-responsive promoter, which drives the expression of a luciferase gene. Treatment of the transfected cells with TGFβ2 or TGFβ3 markedly increased luciferase expression. Addition of sRII reduced the stimulation by TGFβ3 much more significantly than by TGFβ2. On the other hand, sRIII can antagonize the activity of TGFβ2 much better than sRII.

TGFβ2 can form a complex with sRII in the presence of BGe (sRIIIe).

Although TGFβ2 does not interact with sRII (FIG. 1A), it does form a ternary complex with sRII and BGe (sRIIIe) in a native polyacrylamide gel (FIG. 3A). The formation of the ternary complex also requires TGFβ2 since sRII and BGe (sRIIIe) do not form a complex by themselves (FIG. 3B). The presence of TGFβ2, sRII and BGe (sRIIIe) in the ternary complex was confirmed with SDS polyacrylamide gel electrophoresis (FIG. 3C).

BGe and sRII are better and/or broader TGFβ antagonists when used together than sRII or sBG (sRIII) alone.

Figure 4:
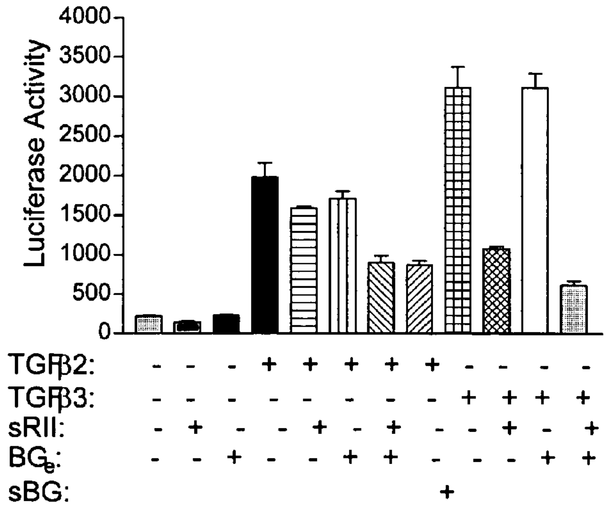
FIG. 4 depicts neutralization of the gene transcription activity of TGFβ2 and TGFβ3 by sRII plus BGe.

While BGe can form a binary complex with TGFβ2 (FIG. 1B), it does not antagonize TGFβ2 activity as shown in FIG. 4. However, when BGe and sRII was used together, they reduced TGFβ2 activity to the same extent as sBG (FIG. 4). Furthermore, BGe and sRII in combination appear more effective than sRII alone in antagonizing TGFβ3 activity, even though BGe (sRIIIe) alone had no effect on TGFβ3 activity. These data suggest that fusion proteins containing sRII and BGe (sRIIIe), BGu (sRIIIu), or sBG (sRIII) may antagonize the three TGFβ isoforms equally well with high binding activity.

Referring now to FIG. 1, binding of the E-domain of betaglycan (BGe) and the TGFβ type II receptor extracellular domain (sRII) to TGFβ2. A. Electrophoretic mobility shift assay in which an increasing amount of sRII has been added to a fixed amount of TGFβ2 and then applied to 12% native polyacryamide gel at pH 8.8. The relative molar amounts of TGFβ2 and sRII used in the assay are indicated above the gel. The protein bands were visualized by Coomassie blue staining. B. Electrophoretic mobility shift assay in which an increasing amount of BGe has been added to a fixed amount of TGFβ2 and then applied to 12% native polyacryamide gel at pH 8.8. The relative molar amounts of TGFβ2 and BGe (sRIIIe) used in the assay are indicated above the gel. The protein bands were visualized by Coomassie blue staining. The arrow labeled BC designates the binary complex formed between TGFβ2 and BGe. C. SDS-PAGE gel demonstrating the identity of the TGFβ2:BGe binary complex formed in the native gel shown in panel B. This was accomplished by excising the band labeled BC from the native gel shown in panel B (right-most lane) and by applying this band to a well of a 12% SDS gel (left-most lane in panel C). Purified TGFβ2 and BGe have also been applied to the SDS gel as controls. Relative molar amounts are indicated above the gel. The protein bands were visualized by Coomassie blue staining. On the basis of the relative amounts of TGFβ2 and BGe (sRIIIe) in the binary complex, together with the relative band intensities for the TGFβ2 and BGe (sRIIIe) controls, we tentatively conclude that BGe and the TGFβ2 homodimer bind with 1:1 stochiometry.

Referring now to FIG. 2, neutralization of the gene transcription activity of TGFβ2 and TGFβ3 by sBG or sRII respectively. Telomerase-immortalized human mammary epithelial cells were plated in a 12-well culture plate at 25,000 cells per well. After 24 hr culture, the cells were transiently co-transfected with a beta-galactosidase (β-gal) expression plasmid and a plasmid containing a TGFβ-responsive promoter and a luciferase gene. Three hours after transfection, the cells were treated with or without TGFβ2 (4 pM), TGFβ3 (4 pM), sRII (20 nM), or sBG (20 nM) as depicted in the figure. The cell lysates were prepared after 20 hr incubation and were used to measure the activities of β-gal and luciferase. The luciferase activity in each cell lysate was normalized by its β-gal activity and plotted in an arbitrary unit. Each bar represents the mean±SE from three independent wells.

Figure 3:
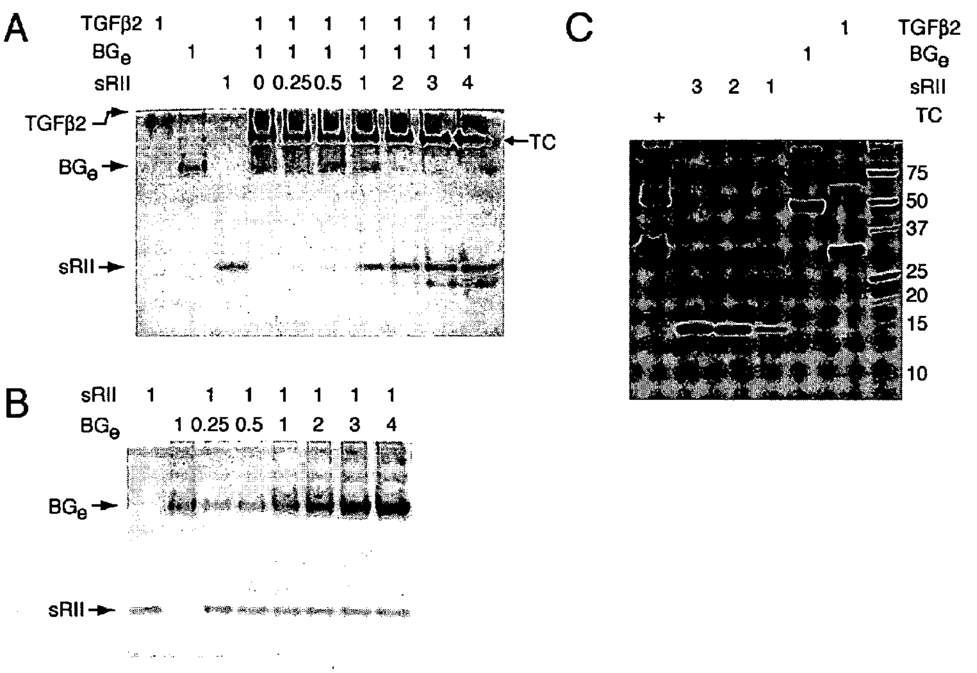
FIGS. 3A-C depict binding of the E-domain of betaglycan (BGe), together with the TGFβ type II receptor extracellular domain (sRII), to TGFβ2.

Referring now to FIG. 3, binding of the E-domain of betaglycan (BGe), together with the TGFβ type II receptor extracellular domain (sRII), to TGFβ2. A. Electrophoretic mobility shift assay in which an increasing amount of sRII has been added to a fixed amount of TGFβ2:BGe binary complex and then applied to 12% native polyacryamide gel at pH 8.8. The relative molar amounts of TGFβ2, BGe, and sRII used in the assay are indicated above the gel. The protein bands were visualized by Coomassie blue staining. The arrow labeled TC designates the ternary complex formed between TGFβ2, BGe, and sRII. B. Electrophoretic mobility shift assay in which an increasing amount of BGe has been added to a fixed amount of sRII and then applied to 12% native polyacryamide gel at pH 8.8. The relative molar amounts of sRII and BGe used in the assay are indicated above the gel. The protein bands were visualized by Coomassie blue staining. C. SDS-PAGE gel demonstrating the identity of the TGFβ2:BGe:sRII ternary complex formed in the native gel shown in panel A. This was accomplished by excising the band labeled TC from the native gel shown in panel A (right-most lane) and by applying this band to a well of a 12% SDS gel (left-most lane in panel C). Purified TGFβ2, BGe, and sRII have also been applied to the SDS gel as controls. Relative molar amounts are indicated above the gel. The protein bands were visualized by Coomassie blue staining. On the basis of the relative amounts of TGFβ2, BGe, sRII in the ternary complex, together with the relative band intensities for the TGFβ2, BGe, and sRII controls, we tentatively conclude that the TGFβ2 homodimer, BGe, and sRII bind with 1:1:1 stochiometry.

Referring now to FIG. 4, neutralization of the gene transcription activity of TGFβ2 and TGFβ3 by sRII plus BGe. Telomerase-immortalized human mammary epithelial cells were plated in a 12-well culture plate at 25,000 cells per well. After 24 hr culture, the cells were transiently co-transfected with a beta-galactosidase (β-gal) expression plasmid and a plasmid containing a TGFβ-responsive promoter and a luciferase gene. Three hours after transfection, the cells were treated with or without TGFβ2 (4 pM), TGFβ3 (4 pM), sRII (20 nM), BGe (20 nM), and/or sBG (20 nM) as depicted in the figure. The cell lysates were prepared after 20 hr incubation and were used to measure the activities of β-gal and luciferase. The luciferase activity in each cell lysate was normalized by its β-gal activity and plotted in an arbitrary unit. Each bar represents the mean±SE from three independent wells.

Referring now to FIGS. 5A-I, several encoding constructs for preparing fusion proteins or polypeptides of this invention are shown to illustrate different types of nucleic acid encoding constructions for forming the fusion proteins of this invention. Looking at FIG. 5A, a DNA construction is shown to include a promoter region A, an sRII encoding region B, which encodes a therapeutically active portion of sRII, an sRIII encoding region C, which encodes a therapeutically active portion of sRIII, and a stop and end region D. Thus, the fusion protein construct of this invention can simply be a fusion protein having a therapeutically active portion of sRII followed by a therapeutically active portion of sRIII. Looking at FIG. 5B, a DNA construction is shown to include a promoter region A, an sRIII encoding region C, which encodes a therapeutically active portion of sRIII, an sRII encoding region B, which encodes a therapeutically active portion of sRII, and a stop and end region D. Thus, the fusion protein construct of this invention can simply be a fusion protein having a therapeutically active portion of sRIII followed by a therapeutically active portion of sRII.

Figure 5A:
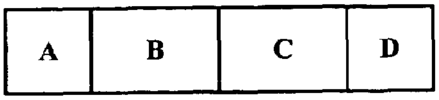
FIGS. 5A-I depict block diagrams of nucleic acid encoding regions of fusion proteins or polypeptides that inhibit TGFβ isoforms.
Figure 5B:
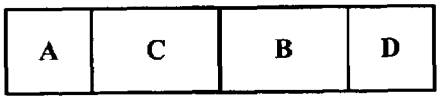
Figure 5C:
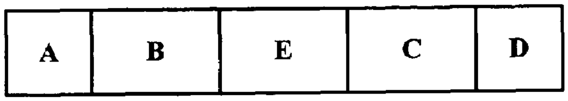
Figure 5D:

Looking at FIG. 5C, a DNA construction is shown to include a promoter region A, an sRII encoding region B, which encodes a therapeutically active portion of sRII, a spacer region E, an sRIII encoding region C, which encodes a therapeutically active portion of sRIII, and a stop and end region D, where the spacer is an inactive amino acid encoding sequence interposed between the two therapeutically active regions to separate them. Thus, the fusion protein construct of this invention can be a fusion protein having a therapeutically active portion of sRII followed by an inactive amino acid sequence and then a therapeutically active portion of sRIII. Looking at FIG. 5D, a DNA construction is shown to include a promoter region A, an sRIII encoding region C, which encodes a therapeutically active portion of sRIII, a spacer region E, an sRII encoding region B, which encodes a therapeutically active portion of sRII, and a stop and end region D, where the spacer is an inactive amino acid encoding sequence interposed between the two therapeutically active regions to separate them. Thus, the fusion protein construct of this invention can be a fusion protein having a therapeutically active portion of sRIII followed by a benign amino acid sequence and then by a therapeutically active portion of sRII.

Figure 5E:
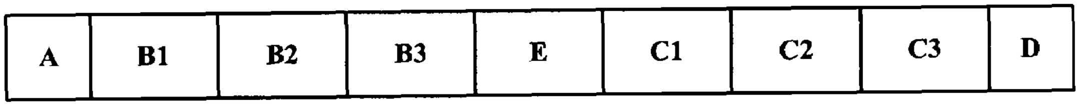
Figure 5F:

Looking at FIG. 5E, a DNA construction is shown to include a promoter region A, three sRII encoding regions B1, B2 and B3, which encode the same or different therapeutically active portions of sRII, an optional benign spacer region E, three sRIII encoding regions C1, C2 and C3, which encode the same or different therapeutically active portions of sRIII, and a stop and end region D. Thus, the fusion protein construct of this invention can be a fusion protein having multiple regions of therapeutically active portions of sRII followed by multiple regions, of therapeutically active portions of sRIII. Looking at FIG. 5F, a DNA construction is shown to include a promoter region A, three sRIII encoding regions C1, C2 and C3, which encode the same or different therapeutically active portions of sRIII, an optional benign spacer region E, three sRII encoding regions B1, B2 and B3, which encode the same or different therapeutically active portions of sRII, and a stop and end region D. Thus, the fusion protein construct of this invention can be a fusion protein having three regions of therapeutically active portions of sRIII followed by three regions of therapeutically active portions of sRII.

Figure 5G:
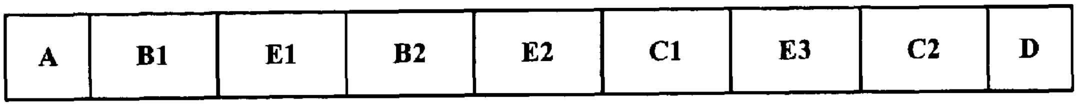

Looking at FIG. 5G, a DNA construction is shown to include a promoter region A, a first sRII encoding regions B1, which encodes a therapeutically active portion of sRII, an optional first spacer region E1, a second sRII encoding regions B2, which encodes the same or different therapeutically active portion of sRII, an optional second benign region E2, a first sRIII encoding region C1, which encodes a therapeutically active portion of sRIII, an optional third benign region E3, a second sRIII encoding region C2, which encodes the same or different therapeutically active portion of sRIII, and a stop and end region D. Thus, the fusion protein construct of this invention can be a fusion protein having multiple regions of therapeutically active portions of sRII followed by multiple regions of therapeutically active portions of sRIII all separated by optional benign regions.

Figure 5H:
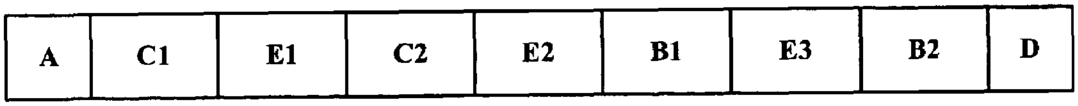

Looking at FIG. 5H, a DNA construction is shown to include a promoter region A, a first sRIII encoding region C1, which encodes a therapeutically active portion of sRIII, an optional first spacer region E1, a second sRIII encoding region C2, which encodes the same or different therapeutically active portion of sRIII, an optional second benign region E2, a first sRII encoding regions B1, which encodes a therapeutically active portion of sRII, an optional third benign region E3, a second sRII encoding regions B2, which encodes the same or different therapeutically active portion of sRII, and a stop and end region D. Thus, the fusion protein construct of this invention can be a fusion protein having multiple regions of therapeutically active portions of sRIII followed by multiple regions of therapeutically active portions of sRII all separated by optional benign regions.

Figure 5I:
Figure 6A:
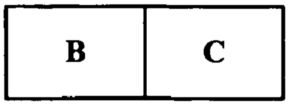
FIGS. 6A-I depict block diagrams of fusion proteins or polypeptides that inhibit TGFβ isoforms.
Figure 6B:
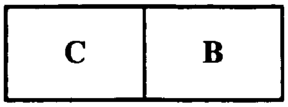
Figure 6C:
Figure 6D:
Figure 6E:
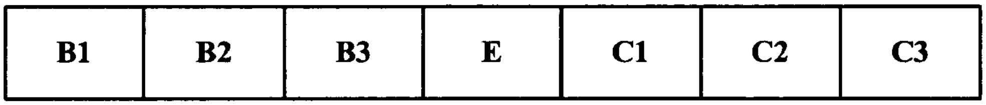
Figure 6F:
Figure 6G:
Figure 6H:
Figure 6I:

Looking at FIG. 5I, a DNA construction is shown to include a promoter region A, a first sRII encoding regions B1, which encodes a therapeutically active portion of sRII, an optional first spacer region E1, a first sRIII encoding region C1, which encodes a therapeutically active portion of sRIII, an optional second benign region E2, a second sRII encoding regions B2, which encodes the same or different therapeutically active portion of sRII, an optional third benign region E3, a second sRIII encoding region C2, which encodes the same or different therapeutically active portion of sRIII, and a stop and end region D. Thus, the fusion protein construct of this invention can be a fusion protein having multiple regions of therapeutically active portions of sRII and therapeutically active portions of sRIII all separated by optional benign regions. It should be recognized by the order of the therapeutically active portions of sRII and sRIII can be as set forth in FIG. 5I or it can be a mixtures of BCs and CBs.

Referring now to FIGS. 6A-I, illustrate the corresponding proteins with amino acid sequences corresponding DNA encoding sequences.

In Vivo Dosing

The inventors believe that the efficacy of using both sRII and BGe (sRIIIe) or any of the fusion proteins containing therapeutically active portions of sRII and therapeutically active portions of sBG (sRIII) to inhibit tumor growth in vivo, based on previous experience with using sBG indicate that sBG can inhibit growth, angiogenesis and metastasis of xenografted human cancer cells in nude mice when administered intraperitoneally in a range of dosing between about 50 nmole/kg every other day and about 200 nmole/kg/day. As such, the inventors believe that this dosing range or lower will be effective for the fusion proteins or when sRII and BGe are administered together in vivo. Thus, a therapeutically active amount of the products and/or fusion proteins of this invention is between about 50 nmole/kg every other day and about 200 nmole/kg/day.

REFERENCES

The following references are cited in shorthand notation throughout the specification:

(Adler et al., 1999) Adler, H. L., McCurdy, M. A., Kattan, M. W., Timme, T. L., Scardino, P. T., and Thompson, T. C. (1999). Elevated levels of circulating interleukin-6 and transforming growth factor-beta1 in patients with metastatic prostatic carcinoma. J. Urol. 161, 182-187.

(Arteaga et al., 1996) Arteaga, C. L., Dugger, T. C., and Hurd, S. D. (1996). The multifunctional role of transforming growth factor (TGF)-beta s on mammary epithelial cell biology. Breast Cancer Res. Treat. 38, 49-56.

(Bandyopadhyay et al., 1999) Bandyopadhyay, A., Zhu, Y., Cibull, M. L., Bao, L. W., Chen, C. G., and Sun, L. Z. (1999). A soluble transforming growth factor beta type III receptor suppresses tumorigenicity and metastasis of human breast cancer MDA-MB-231 cells. Cancer Res. 59, 5041-5046.

(Bandyopadhyay et al., 2002a) Bandyopadhyay, A., Lopez-Casillas, F., Malik, S. N., Montiel, J. L., Mendoza, V., Yang, J., and Sun, L. Z. (2002a). Antitumor Activity of a Recombinant Soluble Betaglycan in Human Breast Cancer Xenograft. Cancer Res. 62, 4690-4695.

(Bandyopadhyay et al., 2002b) Bandyopadhyay, A., Zhu, Y., Malik, S. N., Kreisberg, J., Brattain, M. G., Sprague, E. A., Luo, J., Lopez-Casillas, F., and Sun, L. Z. (2002b). Extracellular domain of TGFbeta type III receptor inhibits angiogenesis and tumor growth in human cancer cells. Oncogene 21, 3541-3551.

(Blobe et al., 2000) Blobe, G. C., Schiemann, W. P., and Lodish, H. F. (2000). Role of transforming growth factor beta in human disease. N. Engl. J. Med. 342, 1350-1358.

(Bonewald and Mundy, 1990) Bonewald, L. F. and Mundy, G. R. (1990). Role of transforming growth factor-beta in bone remodeling. Clin. Orthop. 261-276.

(Chen et al., 1997) Chen, C., Wang, X. F., and Sun, L. Z. (1997). Expression of transforming growth factor beta type III receptor restores autocrine TGF beta1 activity in human breast cancer MCF-7 cells. J. Biol. Chem. 272, 12862-12867.

(Derynck, 1994) Derynck, R. (1994). TGF-beta-receptor-mediated signaling. Trends. Biochem. Sci. 19, 548-553.

(Fajardo et al., 1996) Fajardo, L. F., Prionas, S. D., Kwan, H. H., Kowalski, J., and Allison, A. C. (1996). Transforming growth factor beta1 induces angiogenesis in vivo with a threshold pattern. Lab. Invest. 74, 600-608.

(Fukushima et al., 1993) Fukushima, D., Butzow, R., Hildebrand, A., and Ruoslahti, E. (1993). Localization of transforming growth factor beta binding site in betaglycan. Comparison with small extracellular matrix proteoglycans. J. Biol. Chem. 268, 22710-22715.

(Koeneman et al., 1999) Koeneman, K. S., Yeung, F., and Chung, L. W. (1999). Osteomimetic properties of prostate cancer cells: a hypothesis supporting the predilection of prostate cancer metastasis and growth in the bone environment. Prostate 39, 246-261.

(Lee et al., 1999) Lee, C., Sintich, S. M., Mathews, E. P., Shah, A. H., Kundu, S. D., Perry, K. T., Cho, J. S., Ilio, K. Y., Cronauer, M. V., Janulis, L., and Sensibar, J. A. (1999). Transforming growth factor-beta in benign and malignant prostate. Prostate 39, 285-290.

(Lin et al., 1995) Lin, H. Y., Moustakas, A., Knaus, P., Wells, R. G., Henis, Y. I., and Lodish, H. F. (1995). The soluble exoplasmic domain of the type II transforming growth factor (TGF)-beta receptor. A heterogeneously glycosylated protein with high affinity and selectivity for TGF-beta ligands. J. Biol. Chem. 270, 2747-2754.

(Lopez-Casillas et al., 1993) Lopez-Casillas, F., Wrana, J. L., and Massague, J. (1993). Betaglycan presents ligand to the TGF beta signaling receptor. Cell 73, 1435-1444.

(Lopez-Casillas et al., 1994) Lopez-Casillas, F., Payne, H. M., Andres, J. L., and Massague, J. (1994). Betaglycan can act as a dual modulator of TGF-beta access to signaling receptors: mapping of ligand binding and GAG attachment sites. J. Cell Biol. 124, 557-568.

(Lyons and Moses, 1990) Lyons, R. M. and Moses, H. L. (1990). Transforming growth factors and the regulation of cell proliferation. Eur. J. Biochem. 187, 467-473.

(Markowitz and Roberts, 1996) Markowitz, S. D. and Roberts, A. B. (1996). Tumor suppressor activity of the TGF-beta pathway in human cancers. Cytokine. Growth Factor. Rev. 7, 93-102.

(Massague, 1990) Massague, J. (1990). The transforming growth factor-beta family. Annu. Rev. Cell Biol. 6, 597-641.

(Massague and Chen, 2000) Massague, J. and Chen, Y. G. (2000). Controlling TGF-beta signaling. Genes & Development 14, 627-644.

(Massague et al., 2000) Massague, J., Blain, S. W., and Lo, R. S. (2000). TGFbeta signaling in growth control, cancer, and heritable disorders. Cell 103, 295-309.

(Miyazono et al., 1994) Miyazono, K., ten Dijke, P., Yamashita, H., and Heldin, C. H. (1994). Signal transduction via serine/threonine kinase receptors. Semin. Cell Biol. 5, 389-398.

(Patel et al., 2000) Patel, B. J., Pantuck, A. J., Zisman, A., Tsui, K. H., Paik, S. H., Caliliw, R., Sheriff, S., Wu, L., deKemion, J. B., Tso, C. L., and Belldegrun, A. S. (2000). CL1-GFP: an androgen independent metastatic tumor model for prostate cancer. J. Urol. 164, 1420-1425.

(Piek et al., 1999) Piek, E., Heldin, C. H., and ten Dijke, P. (1999). Specificity, diversity, and regulation in TGF-beta superfamily signaling. FASEB J. 13, 2105-2124.

(Reiss, 1999) Reiss, M. (1999). TGF-beta and cancer. Microbes and Infection 1, 1327-1347.

(Roberts and Spom, 1991) Roberts, A. B. and Spom, M. B. (1991). The transforming growth factor-betas. In Peptide growth factors and their receptors I, M. B. Spom and A. B. Roberts, eds. (Heidelberg: Springer-Verlag), pp. 419-472.

(Roberts and Wakefield, 2003) Roberts, A. B. and Wakefield, L. M. (2003). The two faces of transforming growth factor beta in carcinogenesis. Proc. Natl. Acad. Sci. U.S. A 100, 8621-8623.

(Shariat et al., 2001) Shariat, S. F., Shalev, M., Menesses-Diaz, A., Kim, I. Y., Kattan, M. W., Wheeler, T. M., and Slawin, K. M. (2001). Preoperative plasma levels of transforming growth factor beta(1) (TGF-beta(1)) strongly predict progression in patients undergoing radical prostatectomy. J. Clin. Oncol. 19, 2856-2864.

(Sosroseno and Herminajeng, 1995) Sosroseno, W. and Herminajeng, E. (1995). The immunoregulatory roles of transforming growth factor beta. Br. J. Biomed. Sci. 52, 142-148.

(Vilchis-Landeros et al., 2001) Vilchis-Landeros, M. M., Montiel, L., Mendoza, V., Mendoza-Hernandez, G., and Lopez-Casillas, F. (2001). Recombinant soluble betaglycan is a potent and isoform-selective transforming growth factor-beta neutralizing agent. Biochem. J. 355, 215-222.

(Wang et al., 1991) Wang, X. F., Lin, H. Y., Ng-Eaton, E., Downward, J., Lodish, H. F., and Weinberg, R. A. (1991). Expression cloning and characterization of the TGF-beta type III receptor. Cell 67, 797-805.

(Wang et al., 1999) Wang, X. J., Liefer, K. M., Tsai, S., O'Malley, B. W., and Roop, D. R. (1999). Development of gene-switch transgenic mice that inducibly express transforming growth factor beta1 in the epidermis. Proc. Natl. Acad. Sci. U.S. A 96, 8483-8488.

(Wrana et al., 1994) Wrana, J. L., Attisano, L., Wieser, R., Ventura, F., and Massague, J. (1994). Mechanism of activation of the TGF-beta receptor. Nature 370, 341-347.

(Yang and Moses, 1990) Yang, E. Y. and Moses, H. L. (1990). Transforming growth factor beta 1-induced changes in cell migration, proliferation, and angiogenesis in the chicken chorioallantoic membrane. J. Cell Biol. 111, 731-741.

(Yin et al., 1999) Yin, J. J., Selander, K., Chirgwin, J. M., Dallas, M., Grubbs, B. G., Wieser, R., Massague, J., Mundy, G. R., and Guise, T. A. (1999). TGF-beta signaling blockade inhibits PTHrP secretion by breast cancer cells and bone metastases development. J. Clin. Invest 103, 197-206.

Listing of Sequences Used or Relevant to the Invention

```
SEQ ID NO. 1 sRII DNA Homo sapiens
atgatcccac cgcacgttca gaagtcggtt aataacgaca tgatagtcac tgacaacaac   60

ggtgcagtca agtttccaca actgtgtaaa ttttgtgatg tgagattttc cacctgtgac  120

aaccagaaat cctgcatgag caactgcagc atcacctcca tctgtgagaa gccacaggaa  180

gtctgtgtgg ctgtatggag aaagaatgac gagaacataa cactagagac agtttgccat  240

gaccccaagc tcccctacca tgactttatt ctggaagatg ctgcttctcc aaagtgcatt  300

atgaaggaaa aaaaaaagcc tggtgagact ttcttcatgt gttcctgtag ctctgatgag  360

tgcaatgaca acatcatctt ctcagaagaa tataacacca gcaatcctga ctga        414

SEQ ID NO. 2 sRII Protein Homo sapiens
Met Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

SEQ. ID 3 sBGe (sRIIe) DNA Rattus norvegicus
atgggtagtg gtaccggtcc agagcccagc acccggtgtg aactgtcacc aatcaacgcc   60
```

-continued

```
tctcacccag tccaggcctt gatggagagc ttcaccgttc tgtctggctg tgccagcaga  120

ggcaccaccg ggctgccaag ggaggtccat gtcctaaacc tccgaagtac agatcaggga  180

ccaggccagc ggcagagaga ggttaccctg cacctgaacc ccattgcctc ggtgcacact  240

caccacaaac ctatcgtgtt cctgctcaac tccccccagc ccctggtgtg gcatctgaag  300

acggagagac tggccgctgg tgtccccaga ctcttcctgg tttcagaggg ttctgtggtc  360

cagtttccat caggaaactt ctccttgaca gcagaaacag aggaaaggaa tttccctcaa  420

gaaaatgaac atctgctgcg ctgggcccaa aaggaatatg gagcagtgac ttcgttcacc  480

gaactcaaga tagcaagaaa catctatatt aaagtgggag aagatcaagt gtttcctcct  540

acgtgtaaca tagggaagaa tttcctctca ctcaattacc ttgccgagta ccttcaaccc  600

aaagccgccg aaggttgtgt cctgcccagt caaccccatg aaaaggaagt acacatcatc  660

gagttaatta cccccagctc gaacccttac agcgctttcc aggtggatat aatagttgac  720

atacgacctg ctcaagagga tcccgaggtg gtcaaaaacc ttgtcctgat cttgaagtgc  780

aaaaagtctg tcaactgggt gatcaagtct tttgacgtca agggaaactt gaaagtcatt  840

gctcccaaca gtatcggctt tggaaaagag agtgaacgat ccatgacaat gaccaaattg  900

gtaagagatg acatcccttc cacccaagag aatctgatga agtgggcact ggacaatggc  960

tacaggccag tgacgtcata cacaatggct cccgtggcta atagatttca tcttcggctt 1020

gagaacaacg aggagatgag agatgaggaa gtccacacca ttcctcctga gcttcgtatc 1080

ctgctggacc ctgaccaccc gcccgccctg gacaacccac tcttcccagg agagggaagc 1140

ccaaatggtg gtctcccctt tccattcccg gatga                            1175
```

SEQ. ID 4 sBGe (sRIIe) Protein *Rattus norvegicus*

```
Met Gly Ser Gly Thr Gly Pro Glu Pro Ser Thr Arg Cys Glu Leu Ser
1               5                   10                  15

Pro Ile Asn Ala Ser His Pro Val Gln Ala Leu Met Glu Ser Phe Thr
            20                  25                  30

Val Leu Ser Gly Cys Ala Ser Arg Gly Thr Thr Gly Leu Pro Arg Glu
        35                  40                  45

Val His Val Leu Asn Leu Arg Ser Thr Asp Gln Gly Pro Gly Gln Arg
    50                  55                  60

Gln Arg Glu Val Thr Leu His Leu Asn Pro Ile Ala Ser Val His Thr
65                  70                  75                  80

His His Lys Pro Ile Val Phe Leu Leu Asn Ser Pro Gln Pro Leu Val
                85                  90                  95

Trp His Leu Lys Thr Glu Arg Leu Ala Ala Gly Val Pro Arg Leu Phe
            100                 105                 110

Leu Val Ser Glu Gly Ser Val Val Gln Phe Pro Ser Gly Asn Phe Ser
        115                 120                 125

Leu Thr Ala Glu Thr Glu Glu Arg Asn Phe Pro Gln Glu Asn Glu His
    130                 135                 140

Leu Leu Arg Trp Ala Gln Lys Glu Tyr Gly Ala Val Thr Ser Phe Thr
145                 150                 155                 160

Glu Leu Lys Ile Ala Arg Asn Ile Tyr Ile Lys Val Gly Glu Asp Gln
                165                 170                 175

Val Phe Pro Pro Thr Cys Asn Ile Gly Lys Asn Phe Leu Ser Leu Asn
            180                 185                 190

Tyr Leu Ala Glu Tyr Leu Gln Pro Lys Ala Ala Glu Gly Cys Val Leu
        195                 200                 205

Pro Ser Gln Pro His Glu Lys Glu Val His Ile Ile Glu Leu Ile Thr
    210                 215                 220
```

-continued

```
Pro Ser Ser Asn Pro Tyr Ser Ala Phe Gln Val Asp Ile Ile Val Asp
225                 230                 235                 240

Ile Arg Pro Ala Gln Glu Asp Pro Glu Val Val Lys Asn Leu Val Leu
                245                 250                 255

Ile Leu Lys Cys Lys Lys Ser Val Asn Trp Val Ile Lys Ser Phe Asp
            260                 265                 270

Val Lys Gly Asn Leu Lys Val Ile Ala Pro Asn Ser Ile Gly Phe Gly
        275                 280                 285

Lys Glu Ser Glu Arg Ser Met Thr Met Thr Lys Leu Val Arg Asp Asp
    290                 295                 300

Ile Pro Ser Thr Gln Glu Asn Leu Met Lys Trp Ala Leu Asp Asn Gly
305                 310                 315                 320

Tyr Arg Pro Val Thr Ser Tyr Thr Met Ala Pro Val Ala Asn Arg Phe
                325                 330                 335

His Leu Arg Leu Glu Asn Asn Glu Glu Met Arg Asp Glu Glu Val His
            340                 345                 350

Thr Ile Pro Pro Glu Leu Arg Ile Leu Leu Asp Pro Asp His Pro Pro
        355                 360                 365

Ala Leu Asp Asn Pro Leu Phe Pro Gly Glu Gly Ser Pro Asn Gly Gly
    370                 375                 380

Leu Pro Phe Pro Phe Pro Asp
385                 390
```

SEQ. ID 5 sRII+sBGe DNA *Homo sapiens*

```
atgggtcggg ggctgctcag gggcctgtgg ccgctgcaca tcgtcctgtg gacgcgtatc   60

gccagcacga tcccaccgca cgttcagaag tcggttaata acgacatgat agtcactgac  120

aacaacggtg cagtcaagtt tccacaactg tgtaaatttt gtgatgtgag attttccacc  180

tgtgacaacc agaaatcctg catgagcaac tgcagcatca cctccatctg tgagaagcca  240

caggaagtct gtgtggctgt atggagaaag aatgacgaga acataacact agagacagtt  300

tgccatgacc ccaagctccc ctaccatgac tttattctgg aagatgctgc ttctccaaag  360

tgcattatga aggaaaaaaa aaagcctggt gagactttct tcatgtgttc ctgtagctct  420

gatgagtgca atgacaacat catcttctca gaagaatata acaccagcaa tcctgaccca  480

gagcctggtg cactgtgtga actgtcacct gtcagtgcct cccatcctgt ccaggccttg  540

atggagagct tcactgtttt gtcaggctgt gccagcagag gcacaactgg gctgccacag  600

gaggtgcatg tcctgaatct ccgcactgcg ggccaggggc ctggccagct acagagagag  660

gtcacacttc acctgaatcc catctcctca gtccacatcc accacaagtc tgttgtgttc  720

ctgctcaact ccccacaccc cctggtgtgg catctgaaga cagagagact tgccactggg  780

gtctccagac tgtttttggt gtctgagggt tctgtggtcc agttttcatc agcaaacttc  840

tccttgacag cagaaacaga agaaaggaac ttccccccatg gaaatgaaca tctgttaaat  900

tgggcccgaa aagagtatgg agcagttact tcattcaccg aactcaagat agcaagaaac  960

atttatatta aagtggggga agatcaagtg ttccctccaa agtgcaacat agggaagaat 1020

tttctctcac tcaattacct tgctgagtac cttcaaccca aagcagcaga agggtgtgtg 1080

atgtccagcc agccccagaa tgaggaagta cacatcatcg agctaatcac ccccaactct 1140

aacccctaca gtgctttcca ggtggatata acaattgata taagaccttc tcaagaggat 1200

cttgaagtgg tcaaaaatct catcctgatc ttgaagtgca aaaagtctgt caactgggtg 1260

atcaaatctt ttgatgttaa gggaagcctg aaaattattg ctcctaacag tattggcttt 1320

ggaaaagaga gtgaaagatc tatgacaatg accaaatcaa taagagatga cattccttca 1380
```

-continued acccaaggga atctggtgaa gtgggctttg gacaatggct atagtccaat aacttcatac 1440
acaatggctc ctgtggcaat agtatttcat cttcggcttg aaaataatgc agaggagatg 1500
ggagatgagg aagtccacac tattcctcct gagctacgga tcctgctgga ccctggtgcc 1560
ctgcctgccc tgcagaaccc gcccatccgg ggaggggaag gccaaaatgg aggccttccg 1620
tttcctttcc cagatatttc caggcatcat catcatcatc attag 1665

SEQ. ID 6 sRII+sBGe Protein *Homo sapiens*

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Pro
145                 150                 155                 160

Glu Pro Gly Ala Leu Cys Glu Leu Ser Pro Val Ser Ala Ser His Pro
                165                 170                 175

Val Gln Ala Leu Met Glu Ser Phe Thr Val Leu Ser Gly Cys Ala Ser
            180                 185                 190

Arg Gly Thr Thr Gly Leu Pro Gln Glu Val His Val Leu Asn Leu Arg
        195                 200                 205

Thr Ala Gly Gln Gly Pro Gly Gln Leu Gln Arg Glu Val Thr Leu His
    210                 215                 220

Leu Asn Pro Ile Ser Ser Val His Ile His His Lys Ser Val Val Phe
225                 230                 235                 240

Leu Leu Asn Ser Pro His Pro Leu Val Trp His Leu Lys Thr Glu Arg
                245                 250                 255

Leu Ala Thr Gly Val Ser Arg Leu Phe Leu Val Ser Glu Gly Ser Val
            260                 265                 270

Val Gln Phe Ser Ser Ala Asn Phe Ser Leu Thr Ala Glu Thr Glu Glu
        275                 280                 285

Arg Asn Phe Pro His Gly Asn Glu His Leu Leu Asn Trp Ala Arg Lys
    290                 295                 300

Glu Tyr Gly Ala Val Thr Ser Phe Thr Glu Leu Lys Ile Ala Arg Asn
305                 310                 315                 320

Ile Tyr Ile Lys Val Gly Glu Asp Gln Val Phe Pro Pro Lys Cys Asn
                325                 330                 335

Ile Gly Lys Asn Phe Leu Ser Leu Asn Tyr Leu Ala Glu Tyr Leu Gln
            340                 345                 350

Pro Lys Ala Ala Glu Gly Cys Val Met Ser Ser Gln Pro Gln Asn Glu
        355                 360                 365
```

-continued

```
Glu Val His Ile Ile Glu Leu Ile Thr Pro Asn Ser Asn Pro Tyr Ser
    370                 375                 380

Ala Phe Gln Val Asp Ile Thr Ile Asp Ile Arg Pro Ser Gln Glu Asp
385                 390                 395                 400

Leu Glu Val Val Lys Asn Leu Ile Leu Ile Leu Lys Cys Lys Lys Ser
                405                 410                 415

Val Asn Trp Val Ile Lys Ser Phe Asp Val Lys Gly Ser Leu Lys Ile
            420                 425                 430

Ile Ala Pro Asn Ser Ile Gly Phe Gly Lys Glu Ser Glu Arg Ser Met
        435                 440                 445

Thr Met Thr Lys Ser Ile Arg Asp Asp Ile Pro Ser Thr Gln Gly Asn
    450                 455                 460

Leu Val Lys Trp Ala Leu Asp Asn Gly Tyr Ser Pro Ile Thr Ser Tyr
465                 470                 475                 480

Thr Met Ala Pro Val Ala Ile Val Phe His Leu Arg Leu Glu Asn Asn
                485                 490                 495

Ala Glu Glu Met Gly Asp Glu Glu Val His Thr Ile Pro Pro Glu Leu
            500                 505                 510

Arg Ile Leu Leu Asp Pro Gly Ala Leu Pro Ala Leu Gln Asn Pro Pro
        515                 520                 525

Ile Arg Gly Gly Glu Gly Gln Asn Gly Gly Leu Pro Phe Pro Phe Pro
    530                 535                 540

Asp Ile Ser Arg His His His His His His
545                 550
```

SEQ. ID 7 sRII+sBGu DNA *Homo sapiens*

```
atgggtcggg ggctgctcag ggggcctgtgg ccgctgcaca tcgtcctgtg gacgcgtatc   60

gccagcacga tcccaccgca cgttcagaag tcggttaata acgacatgat agtcactgac  120

aacaacggtg cagtcaagtt tccacaactg tgtaaatttt gtgatgtgag attttccacc  180

tgtgacaacc agaaatcctg catgagcaac tgcagcatca cctccatctg tgagaagcca  240

caggaagtct gtgtggctgt atggagaaag aatgacgaga acataacact agagacagtt  300

tgccatgacc ccaagctccc ctaccatgac tttattctgg aagatgctgc ttctccaaag  360

tgcattatga aggaaaaaaa aaagcctggt gagactttct tcatgtgttc ctgtagctct  420

gatgagtgca atgacaacat catcttctca gaagaatata acaccagcaa tcctgacaga  480

gtctggaatg aagagggaga agatgggctc cctcggccaa aggaccctgt cattcccagc  540

atacaactgt ttcctggtct cagagagcca gaagaggtgc aagggagcgt ggatattgcc  600

ctgtctgtca aatgtgacaa tgagaagatg atcgtggctg tagaaaaaga ttcttttcag  660

gccagtggct actcggggat ggacgtcacc ctgttggatc ctacctgcaa ggccaagatg  720

aatggcacac actttgtttt ggagtctcct ctgaatggct gcggtactcg gccccggtgg  780

tcagcccttg atggtgtggt ctactataac tccattgtga tacaggttcc agcccttggg  840

gacagtagtg gttggccaga tggttatgaa gatctggagt caggtgataa tggatttccg  900

ggagatatgg atgaaggaga tgcttccctg ttcacccgac ctgaaatcgt ggtgtttaat  960

tgcagccttc agcaggtgag gaaccccagc agcttccagg aacagcccca cggaaacatc 1020

accttcaaca tggagctata caacactgac ctctttttgg tgccctccca gggcgtcttc 1080

tctgtgccag agaatggaca cgtttatgtt gaggtatctg ttactaaggc tgaacaagaa 1140

ctgggatttg ccatccaaac gtgctttatc tctccatatt cgaaccctga taggatgtct 1200

cattacacca ttattgagaa tatttgtcct aaagatgaat ctgtgaaatt ctacagtccc 1260
```

-continued

```
aagagagtgc acttccctat cccgcaagct gacatggata agaagcgatt cagctttgtc 1320

ttcaagcctg tcttcaacac ctcactgctc tttctacagt gtgagctgac gctgtgtacg 1380

aagatggaga agcaccccca gaagttgcct aagtgtgtgc ctcctgacga agcctgcacc 1440

tcgctggacg cctcgataat ctgggccatg atgcagaata agaagacgtt caccaagccc 1500

cttgctgtga tccaccatga agcagaatct aaagaaaaag gtccaagcat gaaggaacca 1560

aatccaattt ctccaccaat ttccatggt ctggaccatc atcatcatca tcattag    1617
```

SEQ. ID 8 sRII+sBGu Protein *Homo sapiens*

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Arg
145                 150                 155                 160

Val Trp Asn Glu Glu Gly Glu Asp Gly Leu Pro Arg Pro Lys Asp Pro
                165                 170                 175

Val Ile Pro Ser Ile Gln Leu Phe Pro Gly Leu Arg Glu Pro Glu Glu
            180                 185                 190

Val Gln Gly Ser Val Asp Ile Ala Leu Ser Val Lys Cys Asp Asn Glu
        195                 200                 205

Lys Met Ile Val Ala Val Glu Lys Asp Ser Phe Gln Ala Ser Gly Tyr
    210                 215                 220

Ser Gly Met Asp Val Thr Leu Leu Asp Pro Thr Cys Lys Ala Lys Met
225                 230                 235                 240

Asn Gly Thr His Phe Val Leu Glu Ser Pro Leu Asn Gly Cys Gly Thr
                245                 250                 255

Arg Pro Arg Trp Ser Ala Leu Asp Gly Val Val Tyr Tyr Asn Ser Ile
            260                 265                 270

Val Ile Gln Val Pro Ala Leu Gly Asp Ser Ser Gly Trp Pro Asp Gly
        275                 280                 285

Tyr Glu Asp Leu Glu Ser Gly Asp Asn Gly Phe Pro Gly Asp Met Asp
    290                 295                 300

Glu Gly Asp Ala Ser Leu Phe Thr Arg Pro Glu Ile Val Val Phe Asn
305                 310                 315                 320

Cys Ser Leu Gln Gln Val Arg Asn Pro Ser Ser Phe Gln Glu Gln Pro
                325                 330                 335

His Gly Asn Ile Thr Phe Asn Met Glu Leu Tyr Asn Thr Asp Leu Phe
            340                 345                 350

Leu Val Pro Ser Gln Gly Val Phe Ser Val Pro Glu Asn Gly His Val
```

-continued

```
        355                 360                 365

Tyr Val Glu Val Ser Val Thr Lys Ala Glu Gln Glu Leu Gly Phe Ala
    370                 375                 380

Ile Gln Thr Cys Phe Ile Ser Pro Tyr Ser Asn Pro Asp Arg Met Ser
385                 390                 395                 400

His Tyr Thr Ile Ile Glu Asn Ile Cys Pro Lys Asp Glu Ser Val Lys
                405                 410                 415

Phe Tyr Ser Pro Lys Arg Val His Phe Pro Ile Pro Gln Ala Asp Met
            420                 425                 430

Asp Lys Lys Arg Phe Ser Phe Val Phe Lys Pro Val Phe Asn Thr Ser
        435                 440                 445

Leu Leu Phe Leu Gln Cys Glu Leu Thr Leu Cys Thr Lys Met Glu Lys
    450                 455                 460

His Pro Gln Lys Leu Pro Lys Cys Val Pro Pro Asp Glu Ala Cys Thr
465                 470                 475                 480

Ser Leu Asp Ala Ser Ile Ile Trp Ala Met Met Gln Asn Lys Lys Thr
                485                 490                 495

Phe Thr Lys Pro Leu Ala Val Ile His His Glu Ala Glu Ser Lys Glu
            500                 505                 510

Lys Gly Pro Ser Met Lys Glu Pro Asn Pro Ile Ser Pro Pro Ile Phe
        515                 520                 525

His Gly Leu Asp His His His His His His
    530                 535
```

SEQ. ID 9 sRII+sBG DNA *Homo sapiens*

```
atgggtcggg ggctgctcag ggggctgtgg ccgctgcaca tcgtcctgtg gacgcgtatc   60

gccagcacga tcccaccgca cgttcagaag tcggttaata acgacatgat agtcactgac  120

aacaacggtg cagtcaagtt tccacaactg tgtaaatttt gtgatgtgag attttccacc  180

tgtgacaacc agaaatcctg catgagcaac tgcagcatca cctccatctg tgagaagcca  240

caggaagtct gtgtggctgt atggagaaag aatgacgaga acataacact agagacagtt  300

tgccatgacc ccaagctccc ctaccatgac tttattctgg aagatgctgc ttctccaaag  360

tgcattatga aggaaaaaaa aaagcctggt gagactttct tcatgtgttc ctgtagctct  420

gatgagtgca atgacaacat catcttctca gaagaatata acaccagcaa tcctgaccca  480

gagcctggtg cactgtgtga actgtcacct gtcagtgcct cccatcctgt ccaggccttg  540

atggagagct tcactgtttt gtcaggctgt gccagcagag gcacaactgg gctgccacag  600

gaggtgcatg tcctgaatct ccgcactgcg ggccaggggc ctggccagct acagagagag  660

gtcacacttc acctgaatcc catctcctca gtccacatcc accacaagtc tgttgtgttc  720

ctgctcaact ccccacaccc cctggtgtgg catctgaaga cagagagact tgccactggg  780

gtctccagac tgtttttggt gtctgagggt tctgtggtcc agttttcatc agcaaacttc  840

tccttgacag cagaaacaga agaaaggaac ttcccccatg gaaatgaaca tctgttaaat  900

tgggcccgaa aagagtatgg agcagttact tcattcaccg aactcaagat agcaagaaac  960

atttatatta aagtggggga agatcaagtg ttccctccaa agtgcaacat agggaagaat 1020

tttctctcac tcaattacct tgctgagtac cttcaaccca aagcagcaga agggtgtgtg 1080

atgtccagcc agccccagaa tgaggaagta cacatcatcg agctaatcac ccccaactct 1140

aacccctaca gtgctttcca ggtggatata acaattgata taagaccttc tcaagaggat 1200

cttgaagtgg tcaaaaatct catcctgatc ttgaagtgca aaaagtctgt caactgggtg 1260

atcaaatctt ttgatgttaa gggaagcctg aaaattattg ctcctaacag tattggcttt 1320
```

-continued

```
ggaaaagaga gtgaaagatc tatgacaatg accaaatcaa taagagatga cattccttca 1380

acccaaggga atctggtgaa gtgggctttg gacaatggct atagtccaat aacttcatac 1440

acaatggctc ctgtggcaat agtatttcat cttcggcttg aaaataatgc agaggagatg 1500

ggagatgagg aagtccacac tattcctcct gagctacgga tcctgctgga ccctggtgcc 1560

ctgcctgccc tgcagaaccc gcccatccgg ggaggggaag gccaaaatgg aggccttccg 1620

tttcctttcc cagatatttc caggagagtc tggaatgaag agggagaaga tgggctccct 1680

cggccaaagg accctgtcat tcccagcata caactgtttc ctggtctcag agagccagaa 1740

gaggtgcaag ggagcgtgga tattgccctg tctgtcaaat gtgacaatga gaagatgatc 1800

gtggctgtag aaaaagattc ttttcaggcc agtggctact cggggatgga cgtcaccctg 1860

ttggatccta cctgcaaggc caagatgaat ggcacacact ttgttttgga gtctcctctg 1920

aatggctgcg gtactcggcc ccggtggtca gcccttgatg gtgtggtcta ctataactcc 1980

attgtgatac aggttccagc ccttggggac agtagtggtt ggccagatgg ttatgaagat 2040

ctggagtcag gtgataatgg atttccggga gatatggatg aaggagatgc ttccctgttc 2100

acccgacctg aaatcgtggt gtttaattgc agccttcagc aggtgaggaa ccccagcagc 2160

ttccaggaac agccccacgg aaacatcacc ttcaacatgg agctatacaa cactgacctc 2220

tttttggtgc cctcccaggg cgtcttctct gtgccagaga atggacacgt ttatgttgag 2280

gtatctgtta ctaaggctga acaagaactg ggatttgcca tccaaacgtg ctttatctct 2340

ccatattcga accctgatag gatgtctcat tacaccatta ttgagaatat ttgtcctaaa 2400

gatgaatctg tgaaattcta cagtcccaag agagtgcact tccctatccc gcaagctgac 2460

atggataaga agcgattcag ctttgtcttc aagcctgtct tcaacacctc actgctcttt 2520

ctacagtgtg agctgacgct gtgtacgaag atggagaagc acccccagaa gttgcctaag 2580

tgtgtgcctc ctgacgaagc ctgcacctcg ctggacgcct cgataatctg ggccatgatg 2640

cagaataaga agacgttcac caagcccctt gctgtgatcc accatgaagc agaatctaaa 2700

gaaaaaggtc Caagcatgaa ggaaccaaat ccaatttctc caccaatttt ccatggtctg 2760

gaccatcatc atcatcatca ttag                                        2784
```

SEQ. ID 10 sRII+sBG Protein *Homo sapiens*

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Pro
145                 150                 155                 160
```

-continued

```
Glu Pro Gly Ala Leu Cys Glu Leu Ser Pro Val Ser Ala Ser His Pro
                165                 170                 175

Val Gln Ala Leu Met Glu Ser Phe Thr Val Leu Ser Gly Cys Ala Ser
            180                 185                 190

Arg Gly Thr Thr Gly Leu Pro Gln Glu Val His Val Leu Asn Leu Arg
        195                 200                 205

Thr Ala Gly Gln Gly Pro Gly Gln Leu Gln Arg Glu Val Thr Leu His
    210                 215                 220

Leu Asn Pro Ile Ser Ser Val His Ile His His Lys Ser Val Val Phe
225                 230                 235                 240

Leu Leu Asn Ser Pro His Pro Leu Val Trp His Leu Lys Thr Glu Arg
                245                 250                 255

Leu Ala Thr Gly Val Ser Arg Leu Phe Leu Val Ser Glu Gly Ser Val
            260                 265                 270

Val Gln Phe Ser Ser Ala Asn Phe Ser Leu Thr Ala Glu Thr Glu Glu
        275                 280                 285

Arg Asn Phe Pro His Gly Asn Glu His Leu Leu Asn Trp Ala Arg Lys
    290                 295                 300

Glu Tyr Gly Ala Val Thr Ser Phe Thr Glu Leu Lys Ile Ala Arg Asn
305                 310                 315                 320

Ile Tyr Ile Lys Val Gly Glu Asp Gln Val Phe Pro Pro Lys Cys Asn
                325                 330                 335

Ile Gly Lys Asn Phe Leu Ser Leu Asn Tyr Leu Ala Glu Tyr Leu Gln
            340                 345                 350

Pro Lys Ala Ala Glu Gly Cys Val Met Ser Ser Gln Pro Gln Asn Glu
        355                 360                 365

Glu Val His Ile Ile Glu Leu Ile Thr Pro Asn Ser Asn Pro Tyr Ser
    370                 375                 380

Ala Phe Gln Val Asp Ile Thr Ile Asp Ile Arg Pro Ser Gln Glu Asp
385                 390                 395                 400

Leu Glu Val Val Lys Asn Leu Ile Leu Ile Leu Lys Cys Lys Lys Ser
                405                 410                 415

Val Asn Trp Val Ile Lys Ser Phe Asp Val Lys Gly Ser Leu Lys Ile
            420                 425                 430

Ile Ala Pro Asn Ser Ile Gly Phe Gly Lys Glu Ser Glu Arg Ser Met
        435                 440                 445

Thr Met Thr Lys Ser Ile Arg Asp Asp Ile Pro Ser Thr Gln Gly Asn
    450                 455                 460

Leu Val Lys Trp Ala Leu Asp Asn Gly Tyr Ser Pro Ile Thr Ser Tyr
465                 470                 475                 480

Thr Met Ala Pro Val Ala Ile Val Phe His Leu Arg Leu Glu Asn Asn
                485                 490                 495

Ala Glu Glu Met Gly Asp Glu Glu Val His Thr Ile Pro Pro Glu Leu
            500                 505                 510

Arg Ile Leu Leu Asp Pro Gly Ala Leu Pro Ala Leu Gln Asn Pro Pro
        515                 520                 525

Ile Arg Gly Gly Glu Gly Gln Asn Gly Gly Leu Pro Phe Pro Phe Pro
    530                 535                 540

Asp Ile Ser Arg Arg Val Trp Asn Glu Glu Gly Glu Asp Gly Leu Pro
545                 550                 555                 560

Arg Pro Lys Asp Pro Val Ile Pro Ser Ile Gln Leu Phe Pro Gly Leu
                565                 570                 575

Arg Glu Pro Glu Glu Val Gln Gly Ser Val Asp Ile Ala Leu Ser Val
```

-continued

```
                580                 585                 590

Lys Cys Asp Asn Glu Lys Met Ile Val Ala Val Glu Lys Asp Ser Phe
        595                 600                 605

Gln Ala Ser Gly Tyr Ser Gly Met Asp Val Thr Leu Leu Asp Pro Thr
    610                 615                 620

Cys Lys Ala Lys Met Asn Gly Thr His Phe Val Leu Glu Ser Pro Leu
625                 630                 635                 640

Asn Gly Cys Gly Thr Arg Pro Arg Trp Ser Ala Leu Asp Gly Val Val
                645                 650                 655

Tyr Tyr Asn Ser Ile Val Ile Gln Val Pro Ala Leu Gly Asp Ser Ser
            660                 665                 670

Gly Trp Pro Asp Gly Tyr Glu Asp Leu Glu Ser Gly Asp Asn Gly Phe
        675                 680                 685

Pro Gly Asp Met Asp Glu Gly Asp Ala Ser Leu Phe Thr Arg Pro Glu
    690                 695                 700

Ile Val Val Phe Asn Cys Ser Leu Gln Gln Val Arg Asn Pro Ser Ser
705                 710                 715                 720

Phe Gln Glu Gln Pro His Gly Asn Ile Thr Phe Asn Met Glu Leu Tyr
                725                 730                 735

Asn Thr Asp Leu Phe Leu Val Pro Ser Gln Gly Val Phe Ser Val Pro
            740                 745                 750

Glu Asn Gly His Val Tyr Val Glu Val Ser Val Thr Lys Ala Glu Gln
        755                 760                 765

Glu Leu Gly Phe Ala Ile Gln Thr Cys Phe Ile Ser Pro Tyr Ser Asn
    770                 775                 780

Pro Asp Arg Met Ser His Tyr Thr Ile Ile Glu Asn Ile Cys Pro Lys
785                 790                 795                 800

Asp Glu Ser Val Lys Phe Tyr Ser Pro Lys Arg Val His Phe Pro Ile
                805                 810                 815

Pro Gln Ala Asp Met Asp Lys Lys Arg Phe Ser Phe Val Phe Lys Pro
            820                 825                 830

Val Phe Asn Thr Ser Leu Leu Phe Leu Gln Cys Glu Leu Thr Leu Cys
        835                 840                 845

Thr Lys Met Glu Lys His Pro Gln Lys Leu Pro Lys Cys Val Pro Pro
    850                 855                 860

Asp Glu Ala Cys Thr Ser Leu Asp Ala Ser Ile Ile Trp Ala Met Met
865                 870                 875                 880

Gln Asn Lys Lys Thr Phe Thr Lys Pro Leu Ala Val Ile His His Glu
                885                 890                 895

Ala Glu Ser Lys Glu Lys Gly Pro Ser Met Lys Glu Pro Asn Pro Ile
            900                 905                 910

Ser Pro Pro Ile Phe His Gly Leu Asp His His His His His His
        915                 920                 925
```

SEQ. ID 11 sRII binding sequence A *Homo sapiens*

```
Met Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser
    50
```

SEQ. ID 12 sRII binding sequence *Homo sapiens*

```
Ile Thr Ser Ile Cys Glu Lys Pro Gln Glu Val Cys Val Ala Val Trp
```

-continued

```
1               5                   10                  15

Arg Lys Asn Asp Glu Asn Ile Thr Leu Glu Thr Val Cys His Asp Pro
            20                  25                  30

Lys Leu Pro Tyr His Asp Phe Ile Leu Glu Asp Ala Ala Ser Pro Lys
        35                  40                  45

Cys Ile
    50
```

SEQ. ID 13 sRII binding sequence *Homo sapiens*

```
Met Lys Glu Lys Lys Lys Pro Gly Glu Thr Phe Phe Met Cys Ser Cys
1               5                   10                  15

Ser Ser Asp Glu Cys Asn Asp Asn Ile Ile Phe Ser Glu Glu Tyr Asn
            20                  25                  30

Thr Ser Asn Pro Asp
        35
```

All references cited herein are incorporated by reference herein. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A pharmaceutical composition comprising a therapeutically effective amount of a mixture of:

(a) a soluble type II receptor (sRII) which comprises (i) the extracellular domain of the TGFβ type II receptor or (ii) SEQ ID NO: 2; and (b) a soluble type III receptor (sRIII) which comprises SEQ ID NO: 4.

2. The composition of claim 1, wherein the composition comprises a soluble type II receptor which comprises SEQ ID NO:2.

3. The composition of claim 1, wherein the soluble type II receptor is the extracellular domain of the TGFβ type II receptor.

4. The composition of claim 2, wherein the soluble type II receptor consists of SEQ ID NO: 2.

5. The composition of claim 1, wherein the soluble type III receptor consists of SEQ ID NO: 4.

6. The composition of claim 5, wherein the soluble type II receptor consists of SEQ ID NO: 2.

7. A pharmaceutical composition comprising a therapeutically effective amount of SEQ ID NO: 4.

8. The composition of claim 7, wherein the composition further comprises a therapeutically effective amount of SEQ ID NO:2.

* * * * *

SEQUENCE LISTING

```
<160> NUMBER OF SEQ ID NOS: 13

<210> SEQ ID NO 1
<211> LENGTH: 414
<212> TYPE: DNA
<213> ORGANISM: Homo sapiens
<220> FEATURE:
<221> NAME/KEY: gene
<222> LOCATION: (1)..(414)
<223> OTHER INFORMATION: DNA sequence for the soluble part of the RII
      TGF-beta receptor

<400> SEQUENCE: 1

atgatcccac cgcacgttca gaagtcggtt aataacgaca tgatagtcac tgacaacaac      60

ggtgcagtca agtttccaca actgtgtaaa ttttgtgatg tgagattttc cacctgtgac     120

aaccagaaat cctgcatgag caactgcagc atcacctcca tctgtgagaa gccacaggaa     180

gtctgtgtgg ctgtatggag aaagaatgac gagaacataa cactagagac agtttgccat     240

gaccccaagc tcccctacca tgactttatt ctggaagatg ctgcttctcc aaagtgcatt     300

atgaaggaaa aaaaaaagcc tggtgagact ttcttcatgt gttcctgtag ctctgatgag     360

tgcaatgaca acatcatctt ctcagaagaa tataacacca gcaatcctga ctga           414


<210> SEQ ID NO 2
<211> LENGTH: 137
<212> TYPE: PRT
<213> ORGANISM: Homo sapiens
<220> FEATURE:
<221> NAME/KEY: PEPTIDE
<222> LOCATION: (1)..(137)
<223> OTHER INFORMATION: Polypeptide sequence for sRII

<400> SEQUENCE: 2

Met Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
```

-continued

```
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135
```

<210> SEQ ID NO 3
<211> LENGTH: 1175
<212> TYPE: DNA
<213> ORGANISM: Rattus norvegicus
<220> FEATURE:
<221> NAME/KEY: gene
<222> LOCATION: (1)..(1175)
<223> OTHER INFORMATION: DNA sequence of E domain of BG

<400> SEQUENCE: 3

```
atgggtagtg gtaccggtcc agagcccagc acccggtgtg aactgtcacc aatcaacgcc     60

tctcacccag tccaggcctt gatggagagc ttcaccgttc tgtctggctg tgccagcaga    120

ggcaccaccg ggctgccaag ggaggtccat gtcctaaacc tccgaagtac agatcaggga    180

ccaggccagc ggcagagaga ggttaccctg cacctgaacc ccattgcctc ggtgcacact    240

caccacaaac ctatcgtgtt cctgctcaac tccccccagc ccctggtgtg gcatctgaag    300

acggagagac tggccgctgg tgtccccaga ctcttcctgg tttcagaggg ttctgtggtc    360

cagtttccat caggaaactt ctccttgaca gcagaaacag aggaaaggaa tttccctcaa    420

gaaaatgaac atctgctgcg ctgggcccaa aaggaatatg gagcagtgac ttcgttcacc    480

gaactcaaga tagcaagaaa catctatatt aaagtgggag aagatcaagt gtttcctcct    540

acgtgtaaca tagggaagaa tttcctctca ctcaattacc ttgccgagta ccttcaaccc    600

aaagccgccg aaggttgtgt cctgcccagt caaccccatg aaaaggaagt acacatcatc    660

gagttaatta cccccagctc gaacccttac agcgctttcc aggtggatat aatagttgac    720

atacgacctg ctcaagagga tcccgaggtg gtcaaaaacc ttgtcctgat cttgaagtgc    780

aaaaagtctg tcaactgggt gatcaagtct tttgacgtca agggaaactt gaaagtcatt    840

gctcccaaca gtatcggctt tggaaaagag agtgaacgat ccatgacaat gaccaaattg    900

gtaagagatg acatcccttc cacccaagag aatctgatga agtgggcact ggacaatggc    960

tacaggccag tgacgtcata cacaatggct cccgtggcta atagatttca tcttcggctt   1020

gagaacaacg aggagatgag agatgaggaa gtccacacca ttcctcctga gcttcgtatc   1080

ctgctggacc ctgaccaccc gcccgccctg gacaacccac tcttcccagg agagggaagc   1140

ccaaatggtg gtctcccctt tccattcccg gatga                             1175
```

<210> SEQ ID NO 4
<211> LENGTH: 391
<212> TYPE: PRT

-continued

<213> ORGANISM: Rattus norvegicus
<220> FEATURE:
<221> NAME/KEY: PEPTIDE
<222> LOCATION: (1)..(391)
<223> OTHER INFORMATION: Amino Acid Sequence of the E domain of BG

<400> SEQUENCE: 4

```
Met Gly Ser Gly Thr Gly Pro Glu Pro Ser Thr Arg Cys Glu Leu Ser
1               5                   10                  15

Pro Ile Asn Ala Ser His Pro Val Gln Ala Leu Met Glu Ser Phe Thr
            20                  25                  30

Val Leu Ser Gly Cys Ala Ser Arg Gly Thr Thr Gly Leu Pro Arg Glu
        35                  40                  45

Val His Val Leu Asn Leu Arg Ser Thr Asp Gln Gly Pro Gly Gln Arg
    50                  55                  60

Gln Arg Glu Val Thr Leu His Leu Asn Pro Ile Ala Ser Val His Thr
65                  70                  75                  80

His His Lys Pro Ile Val Phe Leu Leu Asn Ser Pro Gln Pro Leu Val
                85                  90                  95

Trp His Leu Lys Thr Glu Arg Leu Ala Ala Gly Val Pro Arg Leu Phe
            100                 105                 110

Leu Val Ser Glu Gly Ser Val Val Gln Phe Pro Ser Gly Asn Phe Ser
        115                 120                 125

Leu Thr Ala Glu Thr Glu Glu Arg Asn Phe Pro Gln Glu Asn Glu His
    130                 135                 140

Leu Leu Arg Trp Ala Gln Lys Glu Tyr Gly Ala Val Thr Ser Phe Thr
145                 150                 155                 160

Glu Leu Lys Ile Ala Arg Asn Ile Tyr Ile Lys Val Gly Glu Asp Gln
                165                 170                 175

Val Phe Pro Pro Thr Cys Asn Ile Gly Lys Asn Phe Leu Ser Leu Asn
            180                 185                 190

Tyr Leu Ala Glu Tyr Leu Gln Pro Lys Ala Ala Glu Gly Cys Val Leu
        195                 200                 205

Pro Ser Gln Pro His Glu Lys Glu Val His Ile Ile Glu Leu Ile Thr
    210                 215                 220

Pro Ser Ser Asn Pro Tyr Ser Ala Phe Gln Val Asp Ile Ile Val Asp
225                 230                 235                 240

Ile Arg Pro Ala Gln Glu Asp Pro Glu Val Val Lys Asn Leu Val Leu
                245                 250                 255

Ile Leu Lys Cys Lys Lys Ser Val Asn Trp Val Ile Lys Ser Phe Asp
            260                 265                 270

Val Lys Gly Asn Leu Lys Val Ile Ala Pro Asn Ser Ile Gly Phe Gly
        275                 280                 285

Lys Glu Ser Glu Arg Ser Met Thr Met Thr Lys Leu Val Arg Asp Asp
    290                 295                 300

Ile Pro Ser Thr Gln Glu Asn Leu Met Lys Trp Ala Leu Asp Asn Gly
305                 310                 315                 320

Tyr Arg Pro Val Thr Ser Tyr Thr Met Ala Pro Val Ala Asn Arg Phe
                325                 330                 335

His Leu Arg Leu Glu Asn Asn Glu Glu Met Arg Asp Glu Glu Val His
            340                 345                 350

Thr Ile Pro Pro Glu Leu Arg Ile Leu Leu Asp Pro Asp His Pro Pro
        355                 360                 365

Ala Leu Asp Asn Pro Leu Phe Pro Gly Glu Gly Ser Pro Asn Gly Gly
    370                 375                 380
```

-continued

Leu Pro Phe Pro Phe Pro Asp
385 390

<210> SEQ ID NO 5
<211> LENGTH: 1665
<212> TYPE: DNA
<213> ORGANISM: Homo sapiens
<220> FEATURE:
<221> NAME/KEY: misc_recomb
<222> LOCATION: (1)..(1665)
<223> OTHER INFORMATION: DNA sequence encoding a fusion protein of Human sRII and the E domain of BG

<400> SEQUENCE: 5
atgggtcggg ggctgctcag gggcctgtgg ccgctgcaca tcgtcctgtg gacgcgtatc 60
gccagcacga tcccaccgca cgttcagaag tcggttaata acgacatgat agtcactgac 120
aacaacggtg cagtcaagtt tccacaactg tgtaaatttt gtgatgtgag attttccacc 180
tgtgacaacc agaaatcctg catgagcaac tgcagcatca cctccatctg tgagaagcca 240
caggaagtct gtgtggctgt atggagaaag aatgacgaga acataacact agagacagtt 300
tgccatgacc ccaagctccc ctaccatgac tttattctgg aagatgctgc ttctccaaag 360
tgcattatga aggaaaaaaa aaagcctggt gagactttct tcatgtgttc ctgtagctct 420
gatgagtgca atgacaacat catcttctca gaagaatata acaccagcaa tcctgaccca 480
gagcctggtg cactgtgtga actgtcacct gtcagtgcct cccatcctgt ccaggccttg 540
atggagagct tcactgtttt gtcaggctgt gccagcagag gcacaactgg gctgccacag 600
gaggtgcatg tcctgaatct ccgcactgcg ggccaggggc ctggccagct acagagagag 660
gtcacacttc acctgaatcc catctcctca gtccacatcc accacaagtc tgttgtgttc 720
ctgctcaact ccccacaccc cctggtgtgg catctgaaga cagagagact tgccactggg 780
gtctccagac tgtttttggt gtctgagggt tctgtggtcc agttttcatc agcaaacttc 840
tccttgacag cagaaacaga agaaaggaac ttccccccatg gaaatgaaca tctgttaaat 900
tgggcccgaa aagagtatgg agcagttact tcattcaccg aactcaagat agcaagaaac 960
atttatatta aagtgggggga agatcaagtg ttccctccaa agtgcaacat agggaagaat 1020
tttctctcac tcaattacct tgctgagtac cttcaaccca aagcagcaga agggtgtgtg 1080
atgtccagcc agccccagaa tgaggaagta cacatcatcg agctaatcac ccccaactct 1140
aacccctaca gtgctttcca ggtggatata acaattgata taagaccttc tcaagaggat 1200
cttgaagtgg tcaaaaatct catcctgatc ttgaagtgca aaaagtctgt caactgggtg 1260
atcaaatctt ttgatgttaa gggaagcctg aaaattattg ctcctaacag tattggcttt 1320
ggaaaagaga gtgaaagatc tatgacaatg accaaatcaa taagagatga cattccttca 1380
acccaaggga atctggtgaa gtgggctttg gacaatggct atagtccaat aacttcatac 1440
acaatggctc ctgtggcaat agtatttcat cttcggcttg aaaataatgc agaggagatg 1500
ggagatgagg aagtccacac tattcctcct gagctacgga tcctgctgga ccctggtgcc 1560
ctgcctgccc tgcagaaccc gcccatccgg ggaggggaag gccaaaatgg aggccttccg 1620
tttcctttcc cagatatttc caggcatcat catcatcatc attag 1665

<210> SEQ ID NO 6
<211> LENGTH: 554
<212> TYPE: PRT
<213> ORGANISM: Homo sapiens
<220> FEATURE:

-continued

<221> NAME/KEY: PEPTIDE
<222> LOCATION: (1)..(554)
<223> OTHER INFORMATION: A fusion protein of Human sRII and the E domain of BG

<400> SEQUENCE: 6

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Pro
145                 150                 155                 160

Glu Pro Gly Ala Leu Cys Glu Leu Ser Pro Val Ser Ala Ser His Pro
                165                 170                 175

Val Gln Ala Leu Met Glu Ser Phe Thr Val Leu Ser Gly Cys Ala Ser
            180                 185                 190

Arg Gly Thr Thr Gly Leu Pro Gln Glu Val His Val Leu Asn Leu Arg
        195                 200                 205

Thr Ala Gly Gln Gly Pro Gly Gln Leu Gln Arg Glu Val Thr Leu His
    210                 215                 220

Leu Asn Pro Ile Ser Ser Val His Ile His His Lys Ser Val Val Phe
225                 230                 235                 240

Leu Leu Asn Ser Pro His Pro Leu Val Trp His Leu Lys Thr Glu Arg
                245                 250                 255

Leu Ala Thr Gly Val Ser Arg Leu Phe Leu Val Ser Glu Gly Ser Val
            260                 265                 270

Val Gln Phe Ser Ser Ala Asn Phe Ser Leu Thr Ala Glu Thr Glu Glu
        275                 280                 285

Arg Asn Phe Pro His Gly Asn Glu His Leu Leu Asn Trp Ala Arg Lys
    290                 295                 300

Glu Tyr Gly Ala Val Thr Ser Phe Thr Glu Leu Lys Ile Ala Arg Asn
305                 310                 315                 320

Ile Tyr Ile Lys Val Gly Glu Asp Gln Val Phe Pro Pro Lys Cys Asn
                325                 330                 335

Ile Gly Lys Asn Phe Leu Ser Leu Asn Tyr Leu Ala Glu Tyr Leu Gln
            340                 345                 350

Pro Lys Ala Ala Glu Gly Cys Val Met Ser Ser Gln Pro Gln Asn Glu
        355                 360                 365

Glu Val His Ile Ile Glu Leu Ile Thr Pro Asn Ser Asn Pro Tyr Ser
    370                 375                 380
```

-continued

```
Ala Phe Gln Val Asp Ile Thr Ile Asp Ile Arg Pro Ser Gln Glu Asp
385                 390                 395                 400

Leu Glu Val Val Lys Asn Leu Ile Leu Ile Leu Lys Cys Lys Lys Ser
                405                 410                 415

Val Asn Trp Val Ile Lys Ser Phe Asp Val Lys Gly Ser Leu Lys Ile
            420                 425                 430

Ile Ala Pro Asn Ser Ile Gly Phe Gly Lys Glu Ser Glu Arg Ser Met
        435                 440                 445

Thr Met Thr Lys Ser Ile Arg Asp Asp Ile Pro Ser Thr Gln Gly Asn
    450                 455                 460

Leu Val Lys Trp Ala Leu Asp Asn Gly Tyr Ser Pro Ile Thr Ser Tyr
465                 470                 475                 480

Thr Met Ala Pro Val Ala Ile Val Phe His Leu Arg Leu Glu Asn Asn
                485                 490                 495

Ala Glu Glu Met Gly Asp Glu Glu Val His Thr Ile Pro Pro Glu Leu
            500                 505                 510

Arg Ile Leu Leu Asp Pro Gly Ala Leu Pro Ala Leu Gln Asn Pro Pro
        515                 520                 525

Ile Arg Gly Gly Glu Gly Gln Asn Gly Gly Leu Pro Phe Pro Phe Pro
    530                 535                 540

Asp Ile Ser Arg His His His His His His
545                 550
```

<210> SEQ ID NO 7
<211> LENGTH: 1617
<212> TYPE: DNA
<213> ORGANISM: Homo sapiens
<220> FEATURE:
<221> NAME/KEY: misc_recomb
<222> LOCATION: (1)..(1617)
<223> OTHER INFORMATION: DNA sequence encoding a fusion protein of Human sRII and the U domain of BG

<400> SEQUENCE: 7

```
atgggtcggg ggctgctcag gggcctgtgg ccgctgcaca tcgtcctgtg gacgcgtatc     60

gccagcacga tcccaccgca cgttcagaag tcggttaata acgacatgat agtcactgac    120

aacaacggtg cagtcaagtt tccacaactg tgtaaatttt gtgatgtgag attttccacc    180

tgtgacaacc agaaatcctg catgagcaac tgcagcatca cctccatctg tgagaagcca    240

caggaagtct gtgtggctgt atggagaaag aatgacgaga acataacact agagacagtt    300

tgccatgacc ccaagctccc ctaccatgac tttattctgg aagatgctgc ttctccaaag    360

tgcattatga aggaaaaaaa aaagcctggt gagactttct tcatgtgttc ctgtagctct    420

gatgagtgca atgacaacat catcttctca gaagaatata acaccagcaa tcctgacaga    480

gtctggaatg aagagggaga agatgggctc cctcggccaa aggaccctgt cattcccagc    540

atacaactgt ttcctggtct cagagagcca gaagaggtgc aagggagcgt ggatattgcc    600

ctgtctgtca aatgtgacaa tgagaagatg atcgtggctg tagaaaaaga ttcttttcag    660

gccagtggct actcggggat ggacgtcacc ctgttggatc ctacctgcaa ggccaagatg    720

aatggcacac actttgtttt ggagtctcct ctgaatggct gcggtactcg gccccggtgg    780

tcagcccttg atggtgtggt ctactataac tccattgtga tacaggttcc agcccttggg    840

gacagtagtg gttggccaga tggttatgaa gatctggagt caggtgataa tggatttccg    900

ggagatatgg atgaaggaga tgcttccctg ttcacccgac ctgaaatcgt ggtgtttaat    960

tgcagccttc agcaggtgag gaaccccagc agcttccagg aacagcccca cggaaacatc   1020
```

-continued

```
accttcaaca tggagctata caacactgac ctctttttgg tgccctccca gggcgtcttc   1080

tctgtgccag agaatggaca cgtttatgtt gaggtatctg ttactaaggc tgaacaagaa   1140

ctgggatttg ccatccaaac gtgctttatc tctccatatt cgaaccctga taggatgtct   1200

cattacacca ttattgagaa tatttgtcct aaagatgaat ctgtgaaatt ctacagtccc   1260

aagagagtgc acttccctat cccgcaagct gacatggata agaagcgatt cagctttgtc   1320

ttcaagcctg tcttcaacac ctcactgctc tttctacagt gtgagctgac gctgtgtacg   1380

aagatggaga agcacccccca gaagttgcct aagtgtgtgc ctcctgacga agcctgcacc   1440

tcgctggacg cctcgataat ctgggccatg atgcagaata agaagacgtt caccaagccc   1500

cttgctgtga tccaccatga agcagaatct aaagaaaaag gtccaagcat gaaggaacca   1560

aatccaattt ctccaccaat tttccatggt ctggaccatc atcatcatca tcattag      1617
```

<210> SEQ ID NO 8
<211> LENGTH: 538
<212> TYPE: PRT
<213> ORGANISM: Homo sapiens
<220> FEATURE:
<221> NAME/KEY: PEPTIDE
<222> LOCATION: (1)..(538)
<223> OTHER INFORMATION: A fusion protein of Human sRII and the U domain of BG

<400> SEQUENCE: 8

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Arg
145                 150                 155                 160

Val Trp Asn Glu Glu Gly Glu Asp Gly Leu Pro Arg Pro Lys Asp Pro
                165                 170                 175

Val Ile Pro Ser Ile Gln Leu Phe Pro Gly Leu Arg Glu Pro Glu Glu
            180                 185                 190

Val Gln Gly Ser Val Asp Ile Ala Leu Ser Val Lys Cys Asp Asn Glu
        195                 200                 205

Lys Met Ile Val Ala Val Glu Lys Asp Ser Phe Gln Ala Ser Gly Tyr
    210                 215                 220

Ser Gly Met Asp Val Thr Leu Leu Asp Pro Thr Cys Lys Ala Lys Met
225                 230                 235                 240
```

-continued

```
Asn Gly Thr His Phe Val Leu Glu Ser Pro Leu Asn Gly Cys Gly Thr
                245                 250                 255

Arg Pro Arg Trp Ser Ala Leu Asp Gly Val Val Tyr Tyr Asn Ser Ile
            260                 265                 270

Val Ile Gln Val Pro Ala Leu Gly Asp Ser Ser Gly Trp Pro Asp Gly
        275                 280                 285

Tyr Glu Asp Leu Glu Ser Gly Asp Asn Gly Phe Pro Gly Asp Met Asp
    290                 295                 300

Glu Gly Asp Ala Ser Leu Phe Thr Arg Pro Glu Ile Val Val Phe Asn
305                 310                 315                 320

Cys Ser Leu Gln Gln Val Arg Asn Pro Ser Ser Phe Gln Glu Gln Pro
                325                 330                 335

His Gly Asn Ile Thr Phe Asn Met Glu Leu Tyr Asn Thr Asp Leu Phe
            340                 345                 350

Leu Val Pro Ser Gln Gly Val Phe Ser Val Pro Glu Asn Gly His Val
        355                 360                 365

Tyr Val Glu Val Ser Val Thr Lys Ala Glu Gln Glu Leu Gly Phe Ala
    370                 375                 380

Ile Gln Thr Cys Phe Ile Ser Pro Tyr Ser Asn Pro Asp Arg Met Ser
385                 390                 395                 400

His Tyr Thr Ile Ile Glu Asn Ile Cys Pro Lys Asp Glu Ser Val Lys
                405                 410                 415

Phe Tyr Ser Pro Lys Arg Val His Phe Pro Ile Pro Gln Ala Asp Met
            420                 425                 430

Asp Lys Lys Arg Phe Ser Phe Val Phe Lys Pro Val Phe Asn Thr Ser
        435                 440                 445

Leu Leu Phe Leu Gln Cys Glu Leu Thr Leu Cys Thr Lys Met Glu Lys
    450                 455                 460

His Pro Gln Lys Leu Pro Lys Cys Val Pro Pro Asp Glu Ala Cys Thr
465                 470                 475                 480

Ser Leu Asp Ala Ser Ile Ile Trp Ala Met Met Gln Asn Lys Lys Thr
                485                 490                 495

Phe Thr Lys Pro Leu Ala Val Ile His His Glu Ala Glu Ser Lys Glu
            500                 505                 510

Lys Gly Pro Ser Met Lys Glu Pro Asn Pro Ile Ser Pro Pro Ile Phe
        515                 520                 525

His Gly Leu Asp His His His His His His
    530                 535
```

```
<210> SEQ ID NO 9
<211> LENGTH: 2784
<212> TYPE: DNA
<213> ORGANISM: Homo sapiens
<220> FEATURE:
<221> NAME/KEY: misc_comb
<222> LOCATION: (1)..(2784)
<223> OTHER INFORMATION: DNA sequence encoding a fusion protein of Human
      sRII and the sBG

<400> SEQUENCE: 9

atgggtcggg ggctgctcag gggcctgtgg ccgctgcaca tcgtcctgtg gacgcgtatc      60

gccagcacga tcccaccgca cgttcagaag tcggttaata acgacatgat agtcactgac     120

aacaacggtg cagtcaagtt tccacaactg tgtaaatttt gtgatgtgag attttccacc     180

tgtgacaacc agaaatcctg catgagcaac tgcagcatca cctccatctg tgagaagcca     240

caggaagtct gtgtggctgt atggagaaag aatgacgaga acataacact agagacagtt     300
```

-continued

```
tgccatgacc ccaagctccc ctaccatgac tttattctgg aagatgctgc ttctccaaag    360
tgcattatga aggaaaaaaa aaagcctggt gagactttct tcatgtgttc ctgtagctct    420
gatgagtgca atgacaacat catcttctca gaagaatata acaccagcaa tcctgaccca    480
gagcctggtg cactgtgtga actgtcacct gtcagtgcct cccatcctgt ccaggccttg    540
atggagagct tcactgtttt gtcaggctgt gccagcagag gcacaactgg gctgccacag    600
gaggtgcatg tcctgaatct ccgcactgcg ggccaggggc ctggccagct acagagagag    660
gtcacacttc acctgaatcc catctcctca gtccacatcc accacaagtc tgttgtgttc    720
ctgctcaact ccccacaccc cctggtgtgg catctgaaga cagagagact tgccactggg    780
gtctccagac tgtttttggt gtctgagggt tctgtggtcc agttttcatc agcaaacttc    840
tccttgacag cagaaacaga agaaaggaac ttccccccatg gaaatgaaca tctgttaaat    900
tgggcccgaa aagagtatgg agcagttact tcattcaccg aactcaagat agcaagaaac    960
atttatatta aagtgggggga agatcaagtg ttccctccaa agtgcaacat agggaagaat   1020
tttctctcac tcaattacct tgctgagtac cttcaaccca aagcagcaga agggtgtgtg   1080
atgtccagcc agccccagaa tgaggaagta cacatcatcg agctaatcac ccccaactct   1140
aacccctaca gtgctttcca ggtggatata acaattgata taagaccttc tcaagaggat   1200
cttgaagtgg tcaaaaatct catcctgatc ttgaagtgca aaaagtctgt caactgggtg   1260
atcaaatctt ttgatgttaa gggaagcctg aaaattattg ctcctaacag tattggcttt   1320
ggaaaagaga gtgaaagatc tatgacaatg accaaatcaa taagagatga cattccttca   1380
acccaaggga atctggtgaa gtgggctttg gacaatggct atagtccaat aacttcatac   1440
acaatggctc ctgtggcaat agtatttcat cttcggcttg aaaataatgc agaggagatg   1500
ggagatgagg aagtccacac tattcctcct gagctacgga tcctgctgga ccctggtgcc   1560
ctgcctgccc tgcagaaccc gcccatccgg ggaggggaag gccaaaatgg aggccttccg   1620
tttcctttcc cagatatttc caggagagtc tggaatgaag agggagaaga tgggctccct   1680
cggccaaagg accctgtcat tcccagcata caactgtttc ctggtctcag agagccagaa   1740
gaggtgcaag ggagcgtgga tattgccctg tctgtcaaat gtgacaatga gaagatgatc   1800
gtggctgtag aaaaagattc ttttcaggcc agtggctact cggggatgga cgtcaccctg   1860
ttggatccta cctgcaaggc caagatgaat ggcacacact ttgttttgga gtctcctctg   1920
aatggctgcg gtactcggcc ccggtggtca gcccttgatg gtgtggtcta ctataactcc   1980
attgtgatac aggttccagc ccttggggac agtagtggtt ggccagatgg ttatgaagat   2040
ctggagtcag gtgataatgg atttccggga gatatggatg aaggagatgc ttccctgttc   2100
acccgacctg aaatcgtggt gtttaattgc agccttcagc aggtgaggaa ccccagcagc   2160
ttccaggaac agccccacgg aaacatcacc ttcaacatgg agctatacaa cactgacctc   2220
tttttggtgc cctcccaggg cgtcttctct gtgccagaga atggacacgt ttatgttgag   2280
gtatctgtta ctaaggctga acaagaactg ggatttgcca tccaaacgtg ctttatctct   2340
ccatattcga accctgatag gatgtctcat tacaccatta ttgagaatat ttgtcctaaa   2400
gatgaatctg tgaaattcta cagtcccaag agagtgcact tccctatccc gcaagctgac   2460
atggataaga agcgattcag ctttgtcttc aagcctgtct tcaacacctc actgctcttt   2520
ctacagtgtg agctgacgct gtgtacgaag atggagaagc acccccagaa gttgcctaag   2580
tgtgtgcctc ctgacgaagc ctgcacctcg ctggacgcct cgataatctg ggccatgatg   2640
```

-continued

```
cagaataaga agacgttcac caagcccctt gctgtgatcc accatgaagc agaatctaaa   2700

gaaaaaggtc caagcatgaa ggaaccaaat ccaatttctc caccaatttt ccatggtctg   2760

gaccatcatc atcatcatca ttag                                          2784


<210> SEQ ID NO 10
<211> LENGTH: 927
<212> TYPE: PRT
<213> ORGANISM: Homo sapiens
<220> FEATURE:
<221> NAME/KEY: PEPTIDE
<222> LOCATION: (1)..(927)
<223> OTHER INFORMATION: A fusion protein of Human sRII and sBG

<400> SEQUENCE: 10

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Pro
145                 150                 155                 160

Glu Pro Gly Ala Leu Cys Glu Leu Ser Pro Val Ser Ala Ser His Pro
                165                 170                 175

Val Gln Ala Leu Met Glu Ser Phe Thr Val Leu Ser Gly Cys Ala Ser
            180                 185                 190

Arg Gly Thr Thr Gly Leu Pro Gln Glu Val His Val Leu Asn Leu Arg
        195                 200                 205

Thr Ala Gly Gln Gly Pro Gly Gln Leu Gln Arg Glu Val Thr Leu His
    210                 215                 220

Leu Asn Pro Ile Ser Ser Val His Ile His His Lys Ser Val Val Phe
225                 230                 235                 240

Leu Leu Asn Ser Pro His Pro Leu Val Trp His Leu Lys Thr Glu Arg
                245                 250                 255

Leu Ala Thr Gly Val Ser Arg Leu Phe Leu Val Ser Glu Gly Ser Val
            260                 265                 270

Val Gln Phe Ser Ser Ala Asn Phe Ser Leu Thr Ala Glu Thr Glu Glu
        275                 280                 285

Arg Asn Phe Pro His Gly Asn Glu His Leu Leu Asn Trp Ala Arg Lys
    290                 295                 300

Glu Tyr Gly Ala Val Thr Ser Phe Thr Glu Leu Lys Ile Ala Arg Asn
305                 310                 315                 320

Ile Tyr Ile Lys Val Gly Glu Asp Gln Val Phe Pro Pro Lys Cys Asn
```

-continued

```
                325                 330                 335

Ile Gly Lys Asn Phe Leu Ser Leu Asn Tyr Leu Ala Glu Tyr Leu Gln
            340                 345                 350

Pro Lys Ala Ala Glu Gly Cys Val Met Ser Ser Gln Pro Gln Asn Glu
        355                 360                 365

Glu Val His Ile Ile Glu Leu Ile Thr Pro Asn Ser Asn Pro Tyr Ser
    370                 375                 380

Ala Phe Gln Val Asp Ile Thr Ile Asp Ile Arg Pro Ser Gln Glu Asp
385                 390                 395                 400

Leu Glu Val Val Lys Asn Leu Ile Leu Ile Leu Lys Cys Lys Lys Ser
                405                 410                 415

Val Asn Trp Val Ile Lys Ser Phe Asp Val Lys Gly Ser Leu Lys Ile
            420                 425                 430

Ile Ala Pro Asn Ser Ile Gly Phe Gly Lys Glu Ser Glu Arg Ser Met
        435                 440                 445

Thr Met Thr Lys Ser Ile Arg Asp Asp Ile Pro Ser Thr Gln Gly Asn
    450                 455                 460

Leu Val Lys Trp Ala Leu Asp Asn Gly Tyr Ser Pro Ile Thr Ser Tyr
465                 470                 475                 480

Thr Met Ala Pro Val Ala Ile Val Phe His Leu Arg Leu Glu Asn Asn
                485                 490                 495

Ala Glu Glu Met Gly Asp Glu Glu Val His Thr Ile Pro Pro Glu Leu
            500                 505                 510

Arg Ile Leu Leu Asp Pro Gly Ala Leu Pro Ala Leu Gln Asn Pro Pro
        515                 520                 525

Ile Arg Gly Gly Glu Gly Gln Asn Gly Gly Leu Pro Phe Pro Phe Pro
    530                 535                 540

Asp Ile Ser Arg Arg Val Trp Asn Glu Glu Gly Glu Asp Gly Leu Pro
545                 550                 555                 560

Arg Pro Lys Asp Pro Val Ile Pro Ser Ile Gln Leu Phe Pro Gly Leu
                565                 570                 575

Arg Glu Pro Glu Glu Val Gln Gly Ser Val Asp Ile Ala Leu Ser Val
            580                 585                 590

Lys Cys Asp Asn Glu Lys Met Ile Val Ala Val Glu Lys Asp Ser Phe
        595                 600                 605

Gln Ala Ser Gly Tyr Ser Gly Met Asp Val Thr Leu Leu Asp Pro Thr
    610                 615                 620

Cys Lys Ala Lys Met Asn Gly Thr His Phe Val Leu Glu Ser Pro Leu
625                 630                 635                 640

Asn Gly Cys Gly Thr Arg Pro Arg Trp Ser Ala Leu Asp Gly Val Val
                645                 650                 655

Tyr Tyr Asn Ser Ile Val Ile Gln Val Pro Ala Leu Gly Asp Ser Ser
            660                 665                 670

Gly Trp Pro Asp Gly Tyr Glu Asp Leu Glu Ser Gly Asp Asn Gly Phe
        675                 680                 685

Pro Gly Asp Met Asp Glu Gly Asp Ala Ser Leu Phe Thr Arg Pro Glu
    690                 695                 700

Ile Val Val Phe Asn Cys Ser Leu Gln Gln Val Arg Asn Pro Ser Ser
705                 710                 715                 720

Phe Gln Glu Gln Pro His Gly Asn Ile Thr Phe Asn Met Glu Leu Tyr
                725                 730                 735

Asn Thr Asp Leu Phe Leu Val Pro Ser Gln Gly Val Phe Ser Val Pro
            740                 745                 750
```

-continued

Glu Asn Gly His Val Tyr Val Glu Val Ser Val Thr Lys Ala Glu Gln
        755                 760                 765

Glu Leu Gly Phe Ala Ile Gln Thr Cys Phe Ile Ser Pro Tyr Ser Asn
    770                 775                 780

Pro Asp Arg Met Ser His Tyr Thr Ile Ile Glu Asn Ile Cys Pro Lys
785                 790                 795                 800

Asp Glu Ser Val Lys Phe Tyr Ser Pro Lys Arg Val His Phe Pro Ile
                805                 810                 815

Pro Gln Ala Asp Met Asp Lys Lys Arg Phe Ser Phe Val Phe Lys Pro
            820                 825                 830

Val Phe Asn Thr Ser Leu Leu Phe Leu Gln Cys Glu Leu Thr Leu Cys
        835                 840                 845

Thr Lys Met Glu Lys His Pro Gln Lys Leu Pro Lys Cys Val Pro Pro
    850                 855                 860

Asp Glu Ala Cys Thr Ser Leu Asp Ala Ser Ile Ile Trp Ala Met Met
865                 870                 875                 880

Gln Asn Lys Lys Thr Phe Thr Lys Pro Leu Ala Val Ile His His Glu
                885                 890                 895

Ala Glu Ser Lys Glu Lys Gly Pro Ser Met Lys Glu Pro Asn Pro Ile
            900                 905                 910

Ser Pro Pro Ile Phe His Gly Leu Asp His His His His His His
        915                 920                 925

<210> SEQ ID NO 11
<211> LENGTH: 50
<212> TYPE: PRT
<213> ORGANISM: Homo sapiens
<220> FEATURE:
<221> NAME/KEY: BINDING
<222> LOCATION: (1)..(50)
<223> OTHER INFORMATION: Amino acid sequence including AA in the binding region of BG
<220> FEATURE:
<221> NAME/KEY: BINDING
<222> LOCATION: (28)..(28)
<223> OTHER INFORMATION: One of the amino acids identified in a crystal structure as being a binding site of BG
<220> FEATURE:
<221> NAME/KEY: BINDING
<222> LOCATION: (30)..(30)
<223> OTHER INFORMATION: One of the amino acids identified in a crystal structure as being a binding site of BG
<220> FEATURE:
<221> NAME/KEY: BINDING
<222> LOCATION: (32)..(32)
<223> OTHER INFORMATION: One of the amino acids identified in a crystal structure as being a binding site of BG
<220> FEATURE:
<221> NAME/KEY: BINDING
<222> LOCATION: (50)..(50)
<223> OTHER INFORMATION: One of the amino acids identified in a crystal structure as being a binding site of BG

<400> SEQUENCE: 11

Met Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser
    50

-continued

```
<210> SEQ ID NO 12
<211> LENGTH: 50
<212> TYPE: PRT
<213> ORGANISM: Homo sapiens
<220> FEATURE:
<221> NAME/KEY: BINDING
<222> LOCATION: (1)..(50)
<223> OTHER INFORMATION: Amino acid sequence including AA in the binding
      region of BG
<220> FEATURE:
<221> NAME/KEY: BINDING
<222> LOCATION: (1)..(4)
<223> OTHER INFORMATION: Four of the amino acids identified in a crystal
      structure as being a binding site of BG
<220> FEATURE:
<221> NAME/KEY: BINDING
<222> LOCATION: (6)..(6)
<223> OTHER INFORMATION: One of the amino acids identified in a crystal
      structure as being a binding site of BG
<220> FEATURE:
<221> NAME/KEY: BINDING
<222> LOCATION: (28)..(28)
<223> OTHER INFORMATION: One of the amino acids identified in a crystal
      structure as being a binding site of BG

<400> SEQUENCE: 12

Ile Thr Ser Ile Cys Glu Lys Pro Gln Glu Val Cys Val Ala Val Trp
1               5                   10                  15

Arg Lys Asn Asp Glu Asn Ile Thr Leu Glu Thr Val Cys His Asp Pro
            20                  25                  30

Lys Leu Pro Tyr His Asp Phe Ile Leu Glu Asp Ala Ala Ser Pro Lys
        35                  40                  45

Cys Ile
    50


<210> SEQ ID NO 13
<211> LENGTH: 37
<212> TYPE: PRT
<213> ORGANISM: Homo sapiens
<220> FEATURE:
<221> NAME/KEY: BINDING
<222> LOCATION: (1)..(37)
<223> OTHER INFORMATION: Amino acid sequence including AA in the binding
      region of BG
<220> FEATURE:
<221> NAME/KEY: BINDING
<222> LOCATION: (19)..(20)
<223> OTHER INFORMATION: Two of the amino acids identified in a crystal
      structure as being a binding site of BG

<400> SEQUENCE: 13

Met Lys Glu Lys Lys Lys Pro Gly Glu Thr Phe Phe Met Cys Ser Cys
1               5                   10                  15

Ser Ser Asp Glu Cys Asn Asp Asn Ile Ile Phe Ser Glu Glu Tyr Asn
            20                  25                  30

Thr Ser Asn Pro Asp
        35
```